US006241675B1

(12) United States Patent
Smith et al.

(10) Patent No.: US 6,241,675 B1
(45) Date of Patent: Jun. 5, 2001

(54) METHODS AND SYSTEMS FOR DETERMINING VELOCITY OF TISSUE USING THREE DIMENSIONAL ULTRASOUND DATA

(75) Inventors: David W. Smith, Raleigh; Donald K. McAlister; Norman J. Bennett, both of Apex; Paul J. Hilts, Durham; John J. Stefanski, Raleigh; Steve Moore; Richard Holloway, both of Chapel Hill; John A. Schachte, Cary; Ronald E. Hileman; Olaf T. von Ramm, both of Durham; John T. Oxaal, Bahama, all of NC (US)

(73) Assignee: Volumetrics Medical Imaging, Durham, NC (US)

(*) Notice: Subject to any disclaimer, the term of this patent is extended or adjusted under 35 U.S.C. 154(b) by 0 days.

(21) Appl. No.: 09/326,900

(22) Filed: Jun. 7, 1999

Related U.S. Application Data

(60) Provisional application No. 60/088,588, filed on Jun. 9, 1998.

(51) Int. Cl.[7] .................................................. A61B 8/00
(52) U.S. Cl. ............................ 600/443; 600/447; 128/916
(58) Field of Search .................................... 600/443, 447, 600/454, 439; 395/119; 128/916

(56) References Cited

U.S. PATENT DOCUMENTS

| | | |
|---|---|---|
| 4,596,145 | 6/1986 | Smith et al. ............................ 73/626 |
| 4,694,434 | 9/1987 | von Ramm et al. ...................... 367/7 |
| 5,454,371 * | 10/1995 | Fenster et al. ......................... 600/443 |
| 5,474,073 | 12/1995 | Schwartz et al. .................. 128/661.1 |
| 5,485,842 | 1/1996 | Quistgaard .......................... 128/66.07 |
| 5,546,807 | 8/1996 | Oxaal et al. ............................ 73/606 |
| 5,608,849 * | 3/1997 | King, Jr. .............................. 395/119 |
| 5,720,291 | 2/1998 | Schwartz ............................ 128/661.1 |
| 5,860,924 | 1/1999 | Quistgaard ........................... 600/441 |
| 5,876,345 * | 3/1999 | Eaton et al. .......................... 600/466 |
| 5,957,844 * | 9/1999 | Dekel et al. .......................... 600/439 |

OTHER PUBLICATIONS

Jensen, "Estimation of Blood Velocities Using Ultrasound, A Signal Processing Approach" Cambridge University Press, 1996, pp. 194–207.

* cited by examiner

*Primary Examiner*—Marvin M. Lateef
*Assistant Examiner*—Ali M. Imam
(74) *Attorney, Agent, or Firm*—Myers Bigel Sibley & Sajovec

(57) ABSTRACT

A volumetric ultrasound system is used to determine the velocity of tissue using 3D echo data. In particular, the velocity of tissue in a 3D volume is determined by steering ultrasound beams to the tissue in the 3D volume and forming 3D echo data from receive ultrasound beams formed from reflections of the steered ultrasound beams from the tissue in the 3D volume. The velocity of the tissue associated with the 3D echo data can be determined using velocity determination techniques. The velocity of the tissue can be displayed in real-time. For example, in one embodiment, a sub-volume of the 3D volume can be scanned and the determined velocity of the tissue displayed in about 50 milliseconds (ms).

12 Claims, 26 Drawing Sheets

FIG. 11.

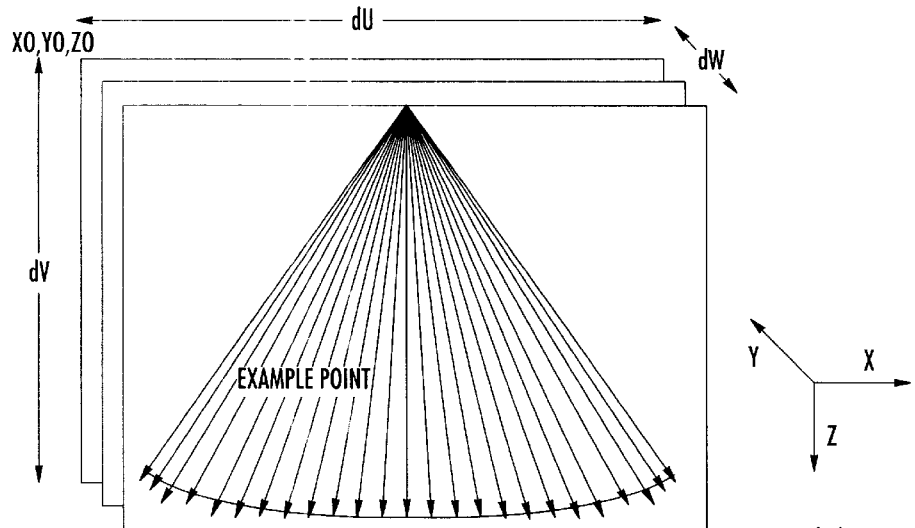

EXAMPLE:
X0,Y0,Z0 = [-400,50,0]   dU,dV,dW = [799,599,0]   ANGULAR SEPARATION IS 0.725 DEGREE (100 LINES)
⟹ ANGLE SCALE = 360/.725 = 496.552 = 0x1f0.8d
SKIN_OFFSET = 83 SAMPLES          RAD MAX = 499 SAMPLES
THETA OFFSET = 50 LIINES          THETA MAX = 79 LIINES
PHI OFFSET = 40 LINES             PHI MAX = 79 LINES dXdU = .75
dXdV = 0
dXdW = N/A (0)
dYdU = 0
dYdV = 0
dYdW = N/A (0)
dZdU = 0
dZdV = 1.25
dZdW = N/A (0)

NOTE: THE THETA, PHI MAX IS THE ABSOLUTE DISTANCE BETWEEN THETA, PHI MIN/MAX

NEXT SEQUENCER SCAN POINT: X,Y,Z = [-111,50,400] THIS IS SCAN POINT: 800*400/1.25+(400-111+1))/.725=256, 400TH POINT PROCESSED

R=418.116                               ~418(30/256)SAMPLES
Θ=tan$^{-1}$(-111/400)=-15.509deg. ~-15.(130/256)DEGREES ⟹ -2823/65536 UNIT CIRCLES FROM TMC2330
Φ=tan$^{-1}$(50/400)= 7.125deg. ~ 7.(32/256)DEGREES ⟹ 1297/65536 UNIT CIRCLES FROM TMC2330

CONVERT (Θ,Φ) TO ADDRESS:
R = 418.(30/256) - SKIN_OFFSET = 335.(30/256)      =0x14f.1e  ADDR UNITS
Θ = -2823 * ANGLE SCALE= 0x15.64 + THETA OFFSET (0x32) = 0X1c.9c   ADDR UNITS (LINES)
Φ = 1297 * ANGLE SCALE = 0x09.d4 + PHI OFFSET (0x28) = 0x31.d4   ADDR UNITS (LINES)
   BOTH R,Θ AND Φ ARE LESS THAN THE MAX R,Θ AND Φ ARE GREATER THAN 0 SO NO CLIPPING IS APPLIED

PHYSICAL ADDRESS DISTRIBUTION:
R = 0x14f.1e ⟹ EVEN/ODD ADDR = 0x42/0x41,          RAD MUX SEL = 6   AND RAD COEF = 0xda
Θ = 0x1c.9c ⟹ ROW0/1/2/3 ADDR = 0x07/0x07/0x07/0x06, Θ MUX = 3       AND THETA COEF = 0x9c
Φ = 0x31.d4 ⟹ ROW0/1/2/3 ADDR = 0x0c/0x0c/0x0c/0x0c, Φ MUX = 0       AND PHI COEF = 0xd4

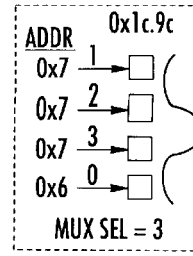

*FIG. 17.*

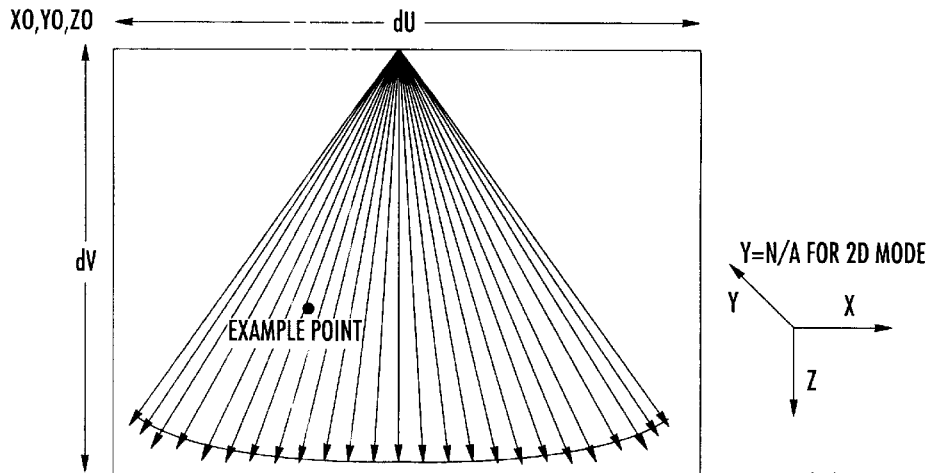

EXAMPLE:
X0,Y0,Z0 = [-400,0,0]   dU,dV,dW = [799,599,0]   ANGULAR SEPARATION IS 0.105 DEGREE (600 LINES)
⟹ ANGLE SCALE = 360/.105 = 3428.57 = 0xd64.92
SKIN_OFFSET = 80 SAMPLES       RAD MAX = 1000 SAMPLES
THETA OFFSET = 364 LIINES       THETA MAX = 600 LINES
PHI OFFSET = N/A                N/A79 LINES $dXdU = .725$
$dXdV = 0$
$dXdW = N/A\ (0)$
$dYdU = 0$
$dYdV = 0$
$dYdW = N/A\ (0)$
$dZdU = 0$
$dZdV = 1.25$
$dZdW = N/A\ (0)$

NOTE: THE THETA, PHI MAX IS THE ABSOLUTE DISTANCE BETWEEN THETA, PHI MIN/MAX

NEXT SEQUENCER SCAN POINT: X,Y,Z = [111,0,400] THIS IS SCAN POINT: 800*400/1.25+(400-111+1))/.725=256,
400TH POINT PROCESSED
    R=415.116                    ~415(30/256)SAMPLES
    $\Theta = \tan^{-1}(-111/400) = -15.509\deg$. ~15.(130/256)DEGREES ⟹ 2823/65536 UNIT CIRCLES FROM TMC2330
    $\Phi = \tan^{-1}(0/400) = 0$ CONVERT (Θ,Φ) TO ADDRESS:
    R = 415.(30/256) - SKIN_OFFSET = 335.(30/256)     =0x14f.1e ADDR UNITS
    Θ = -2823 * ANGLE SCALE= 0x93.b0 + THETA OFFSET (0x16c) = 0X1ff.b0 ADDR UNITS (LINES)
    Φ = 0 * ANGLE SCALE = 0x00.00 ADDR UNITS
    BOTH R,AND Θ ARE LESS THAN THE MAX R AND Θ AND GREATER THAN 0 SO NO CLIPPING IS APPLIED PHYSICAL ADDRESS DISTRIBUTION:
    R = 0x14f.1e ⟹ EVEN/ODD ADDR = 0x42/0x41,           RAD MUX SEL = 6  AND RAD COEF = 0xda
    Θ = 0x1ff.f2 ⟹ ROW0/1/2/3 ADDR = 0x20/0x20/0x1f/0x1f, Θ MUX = 2   AND THETA COEF = 0xf2
    Φ = Θ EXTENSION ⟹ " ADDR = 0x1/0x1/0x0/0x0                        AND PHI COEF = 0xe

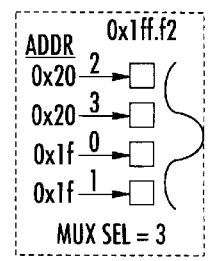

METHODS AND SYSTEMS FOR DETERMINING VELOCITY OF TISSUE USING THREE DIMENSIONAL ULTRASOUND DATA

CROSS REFERENCR TO RELATED APPLICATION

This application claims the benefit of provisional application serial no. 60/088,588, filed Jun. 9, 1998, entitled "Methods and Systems for Measuring Velocity of Tissue Using Doppler Beams Within Volumetric Ultrasound Images" which is incorporated herein by reference.

FIELD OF THE INVENTION

The present invention relates to the field of ultrasound imaging in general, and more particularly, to velocity determinations of tissue using ultrasound imaging.

BACKGROUND OF THE INVENTION

Medical ultrasound has gained increased popularity as a diagnostic tool. A number of techniques for estimating the velocity of biological tissue using ultrasonic energy have been investigated, and some of these techniques are now considered standard clinical practice. For example, Doppler ultrasound techniques have been used to estimate the velocity of blood flow for some time by processing echoes generated by multiple transmissions and receptions of ultrasonic energy formed into a beam that can be steered in the region being investigated to measure frequency or phase shift.

Doppler techniques, however, may produce inaccurate results if the Doppler beam is not steered accurately. Accurately steering the Doppler beam may be difficult, however, when using a conventional two dimensional (2D) ultrasound scan. For example, a conventional 2D ultrasound system may produce a B slice image that represents a slice of the region being imaged. Unfortunately, the operator may experience difficulty in accurately steering the Doppler beam to the desired portion of a region using the conventional B slice which may reduce the accuracy of the estimated velocity of the biological tissue or affect estimates relating to the extent of the condition being examined. For example, if the Doppler beam is not steered to the desired portion of a heart valve being imaged, the determined size of the hole in heart valve may be wrong or the velocity of a jet due to a hole in the heart valve may be inaccurate.

In view of the above, there is a need to allow improved methods and systems for estimating the velocity of tissue using Doppler ultrasound techniques.

SUMMARY OF THE INVENTION

It is, therefore, an object of the present invention to allow improved methods and systems for determining the velocity of tissue.

It is another object of the present invention to allow improved targeting of tissue for velocity determinations.

These and other object are provided by volumetric ultrasound systems that determine the velocity of tissue in a 3D volume by steering ultrasound beams to the tissue in the 3D volume and forming 3D echo data from receive ultrasound beams formed from reflections of the steered ultrasound beams from the tissue in the 3D volume. The velocity of the tissue associated with the 3D echo data can be determined using velocity determination techniques. The velocity of the tissue can be displayed in real-time. For example, in one embodiment, a sub-volume of the 3D volume can be scanned and the determined velocity of the tissue displayed in about 50 milliseconds (ms). The display of the tissue velocity can comprise a Color Flow Doppler (CF) display, a Pulse Wave Doppler (PW) display and/or a Continuous Wave Doppler (CW) display. In an alternate embodiment, the 3D echo data is used to create a Motion Mode (M mode) display, wherein the display represents the relative displacement of the tissue being scanned.

In another aspect of the present invention, first tissue in the 3D volume is targeted using a display of a first image at a first position in the 3D volume. Second tissue in the 3D volume is targeted at a second position in the 3D volume and the display of the first image at the first position in the 3D volume is changed to a second image at a third position in the 3D volume based on the second position in the 3D volume. Accordingly, the user may target the tissue under investigation more accurately.

BRIEF DESCRIPTION OF THE FIGURES

Figure 11:
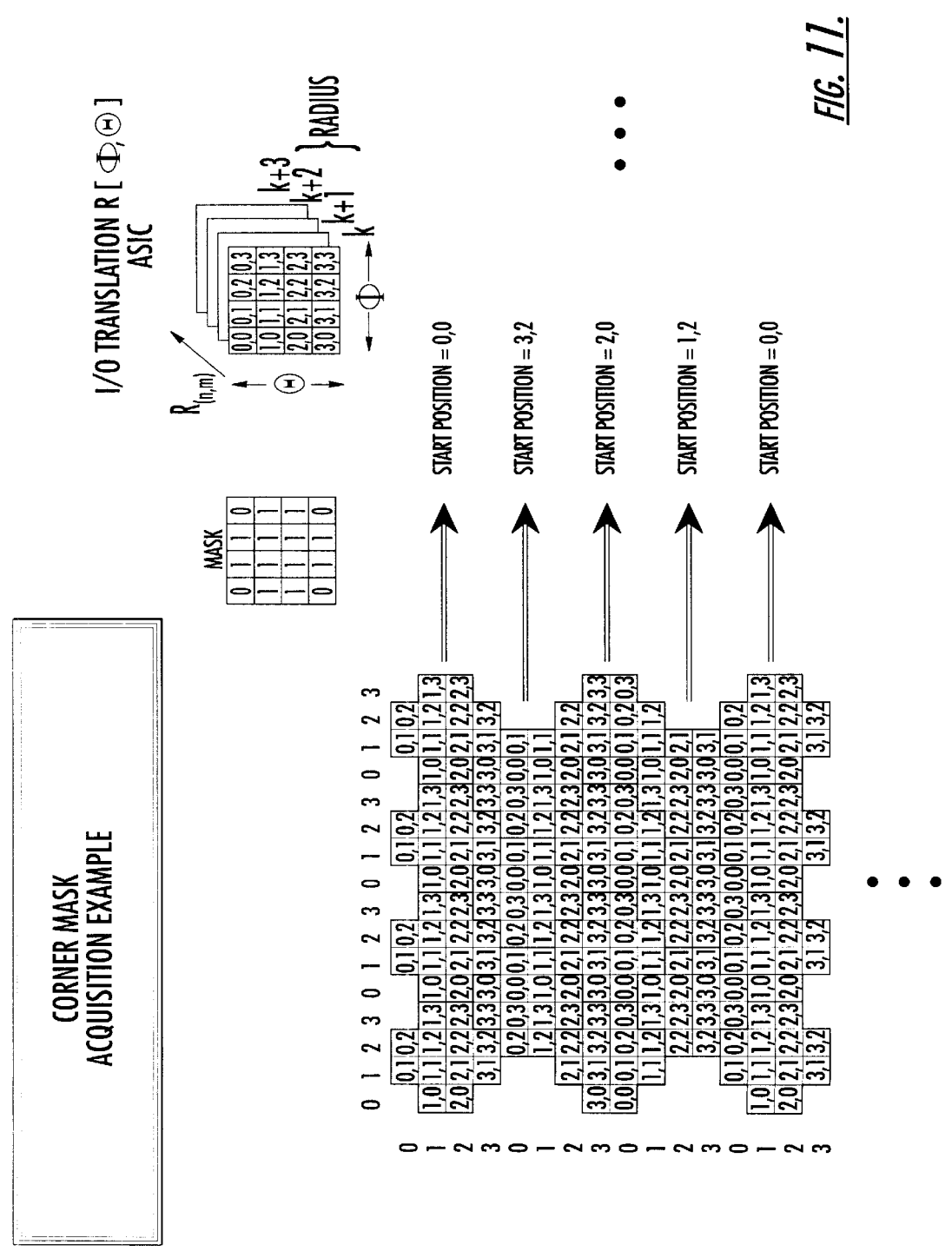

FIG. 11 is an exemplary illustration of comer mask acquisition according to the present invention;

FIGS. 17 and 18 illustrate exemplary operation of the output address generator of FIG. 14 for a specific scan point.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As will be appreciated by one of skill in the art, the present invention may be embodied as methods or devices. Accordingly, the present invention may take the form of an entirely hardware embodiment, an entirely software embodiment or an embodiment combining software and hardware aspects.

The present invention is also described using a flow chart illustration and block diagrams. It will be understood that each block of the flowchart illustrations and block diagrams, and combinations of blocks in the flowchart illustrations and blocks of the block diagrams, can be implemented by computer program instructions. These program instructions may be provided to a processor(s) within a volumetric ultrasound system, such that the instructions which execute on the processor(s) create means for implementing the functions specified in the flowchart or block diagram blocks. The computer program instructions may be executed by the processor(s) to cause a series of operational steps to be performed by the processor(s) to produce a computer implemented process such that the instructions which execute on the processor(s) provide steps for implementing the functions specified in the flowchart or block diagram blocks.

Accordingly, blocks of the flowchart illustrations and block diagrams support combinations of means for performing the specified functions, combinations of steps for performing the specified functions and program instruction means for performing the specified functions. It will also be understood that each block of the flowchart illustrations, and combinations of blocks in the flowchart illustrations and blocks in the block diagrams, can be implemented by special purpose hardware-based systems which perform the specified functions or steps, or combinations of special purpose hardware and computer instructions.

3D Echo Data Formation

Figure 1A:
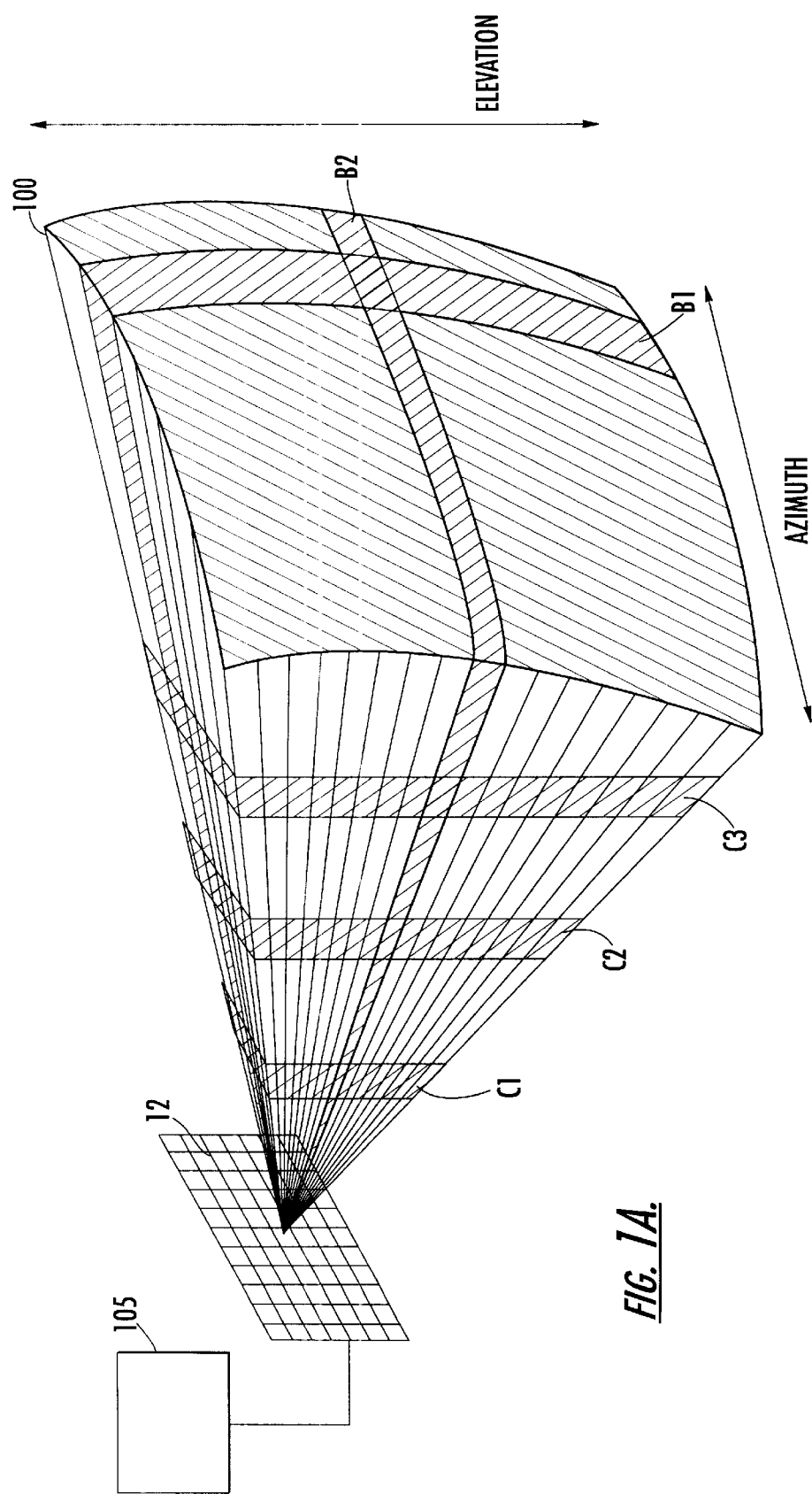
FIG. 1A is a perspective view of a 3D volume scanned by volumetric ultrasound systems and methods according to the present invention.

FIG. 1A illustrates a three dimensional (3D) volume 100 of a body scanned according to the present invention. The 3D volume 100 is scanned by a volumetric ultrasound system 105 coupled to an transducer array 12. Volumetric ultrasound systems and volumetric scanning techniques are described, for example, in U.S. Pat. No. 5,546,807 to Oxaal et al. entitled "High Speed Volumetric Ultrasound Imaging System" and U.S. Pat. No. 4,596,145 to Smith et al. entitled "Acoustic Orthoscopic Imaging System" both of which are commonly assigned to the present assignee and are both incorporated herein by reference.

The volumetric ultrasound system 105 can be used to determine the velocity of tissue in the body using Doppler techniques. It will be understood, however, that the velocity of the tissue can be determined using techniques other than Doppler techniques, such as correlation techniques or other velocity determination techniques known to those having skill in the art. As used herein, the term "tissue" includes biological tissue in a body such as blood. For example, the present invention can be used to measure the velocity of blood in a region of the body such as a heart.

Figure 1B:
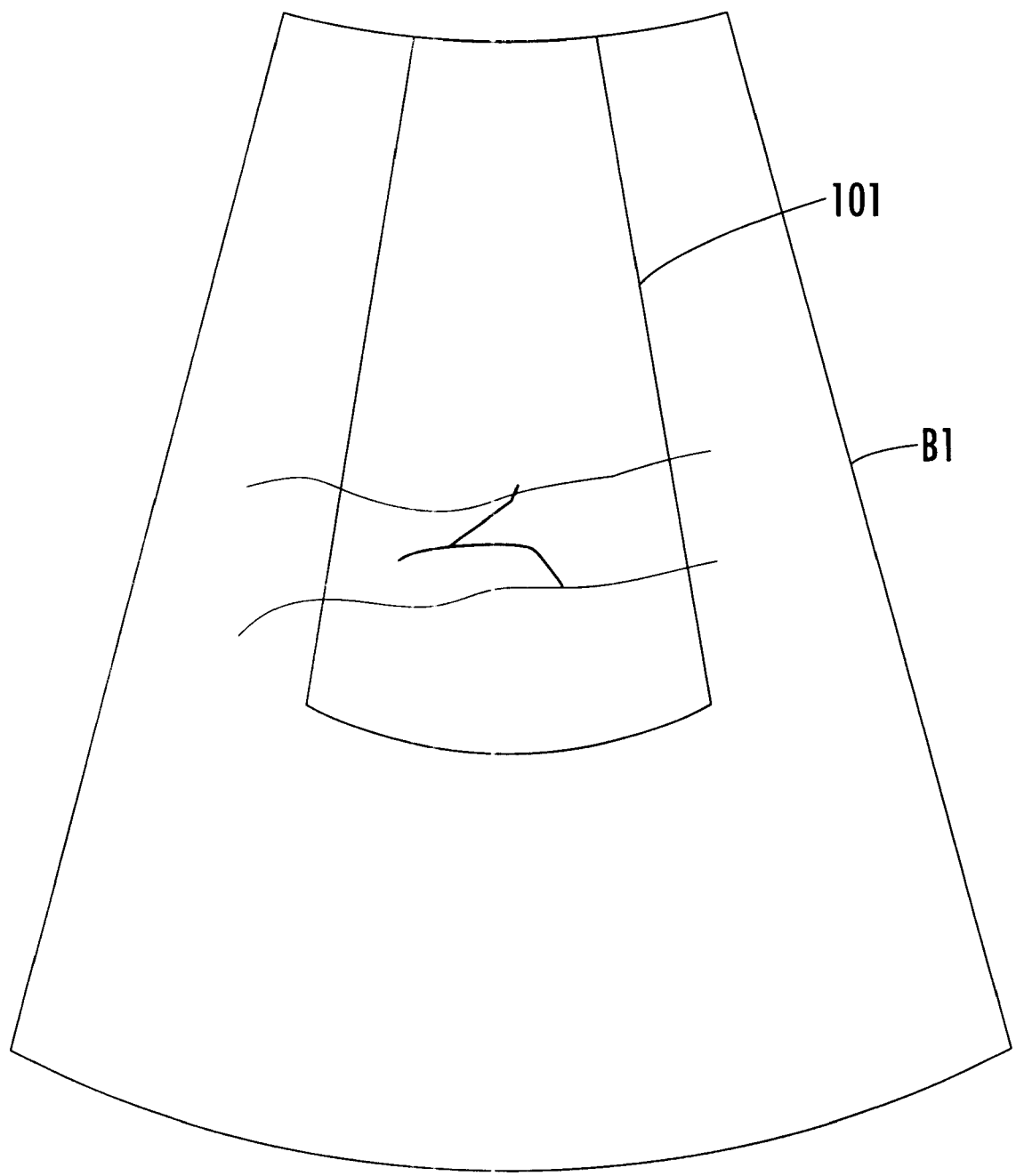
FIG. 1B is a diagram of a sub-volume included in a slice of the 3D volume shown in FIG. 1A.
Figure 1C:
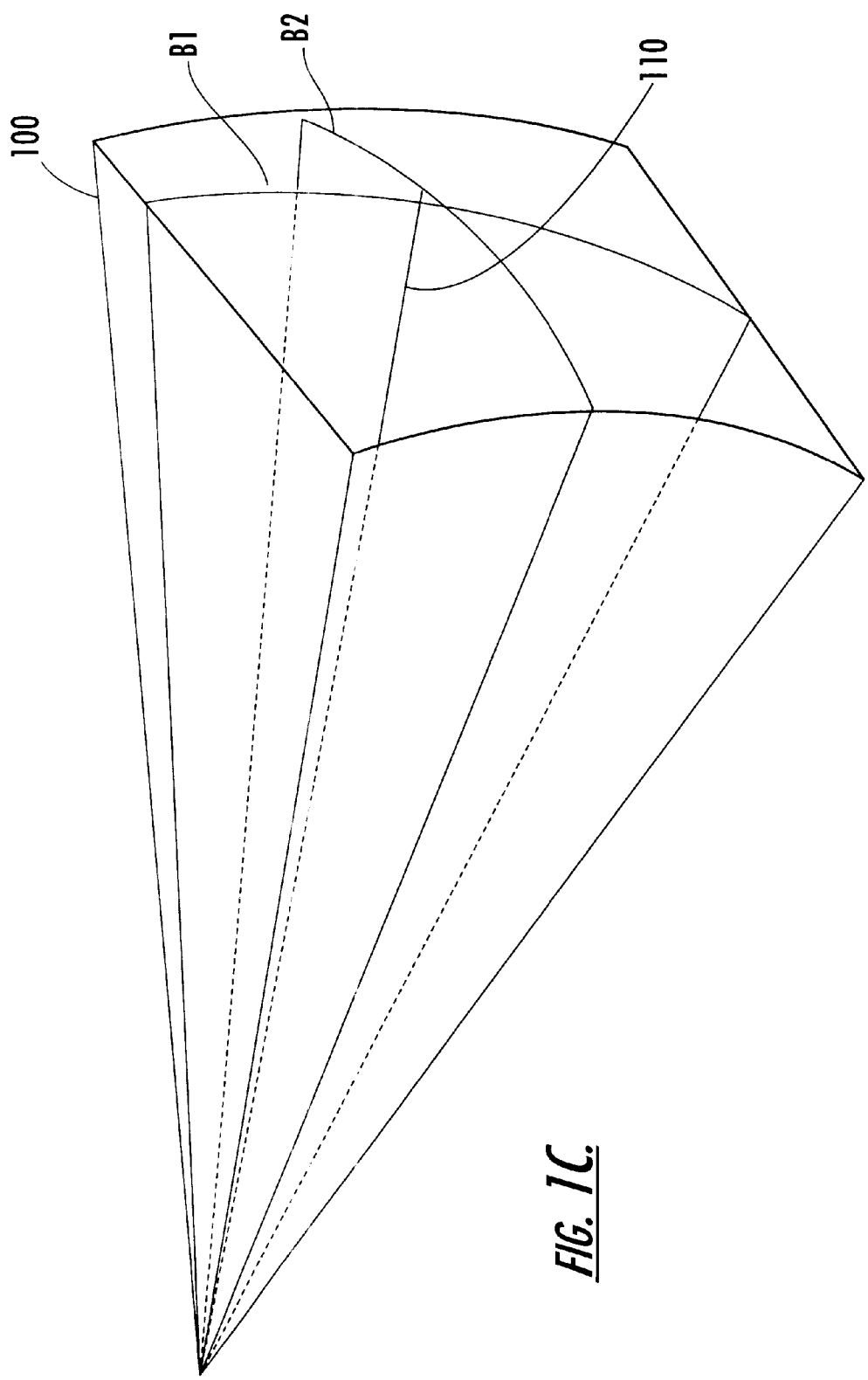
FIG. 1C is a perspective view of a 3D volume including first and second B slices and an intersecting line thereof.
Figure 1D:
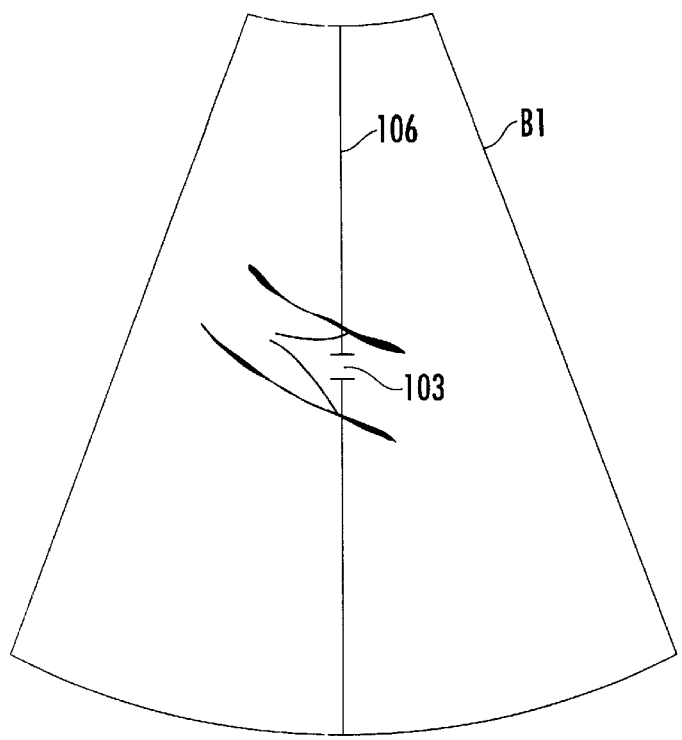
FIGS. 1D through 1G are views of aiming lines used to determine velocity of tissue in the 3D volume according to the present invention.
Figure 1E:
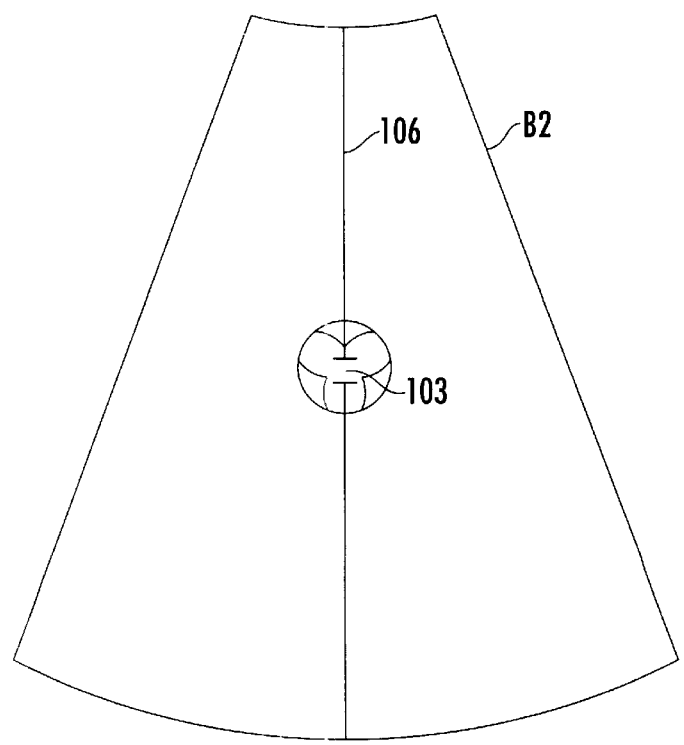
Figure 1F:
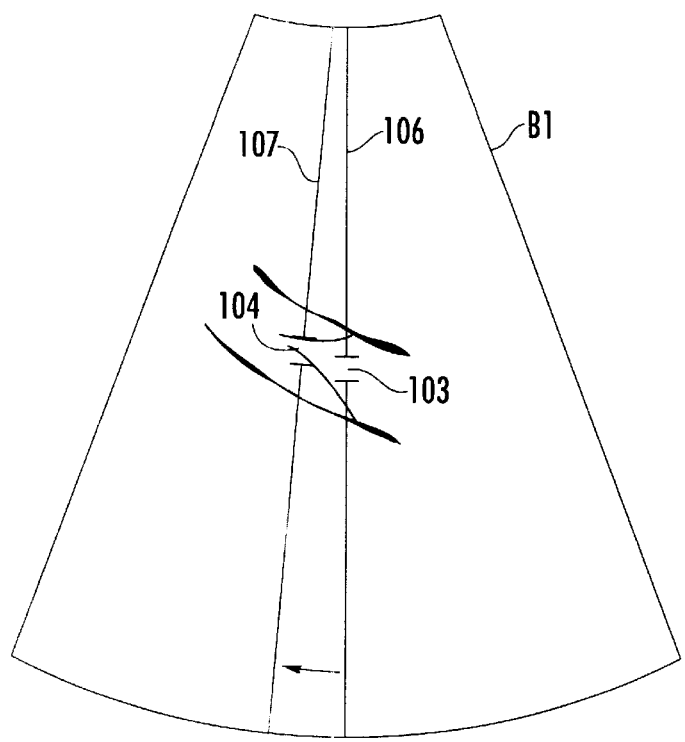
Figure 1G:
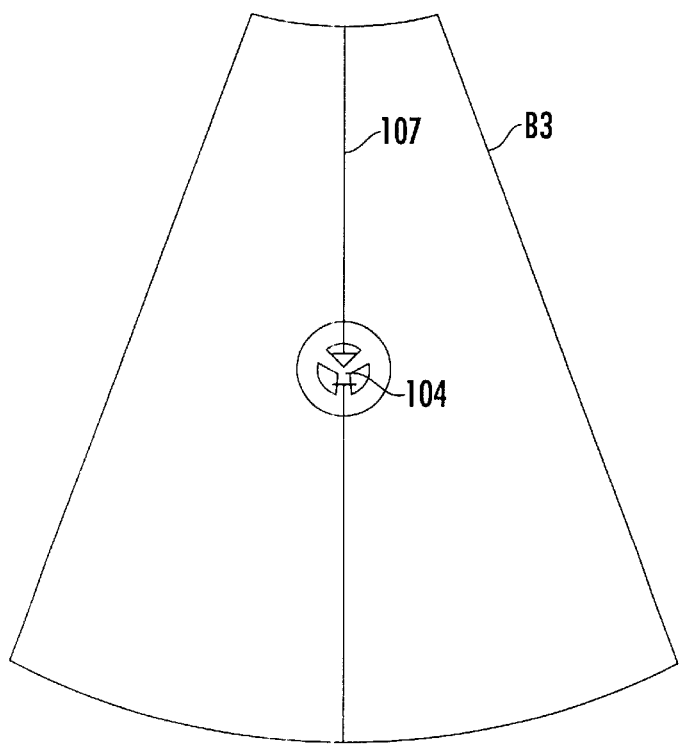
Figure 1H:
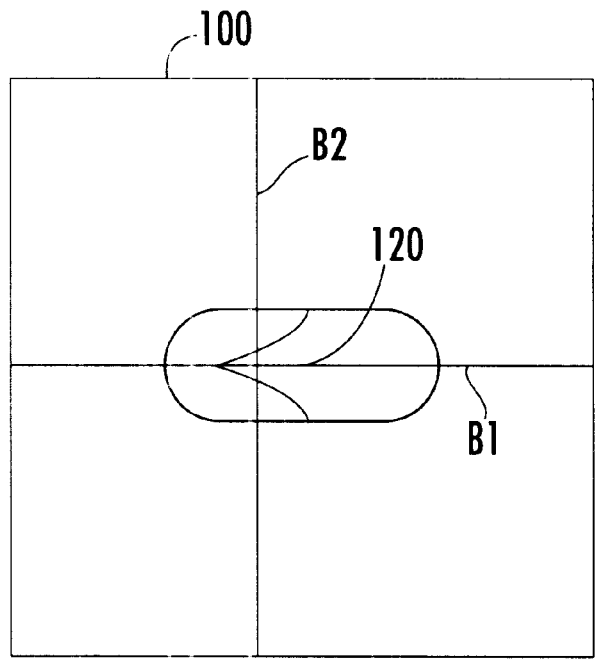
FIGS. 1H and 1I are front views of the 3D volume shown in FIG. 1A including B slices generated according to the present invention.
Figure 1I:
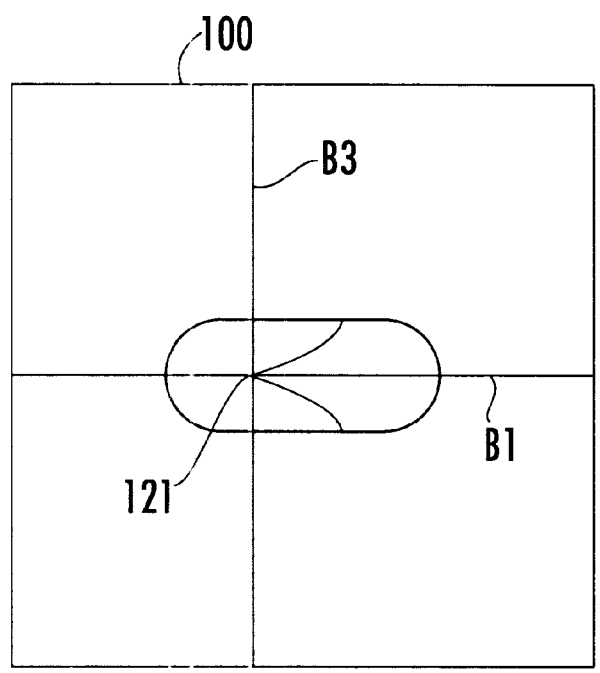
Figure 1J:
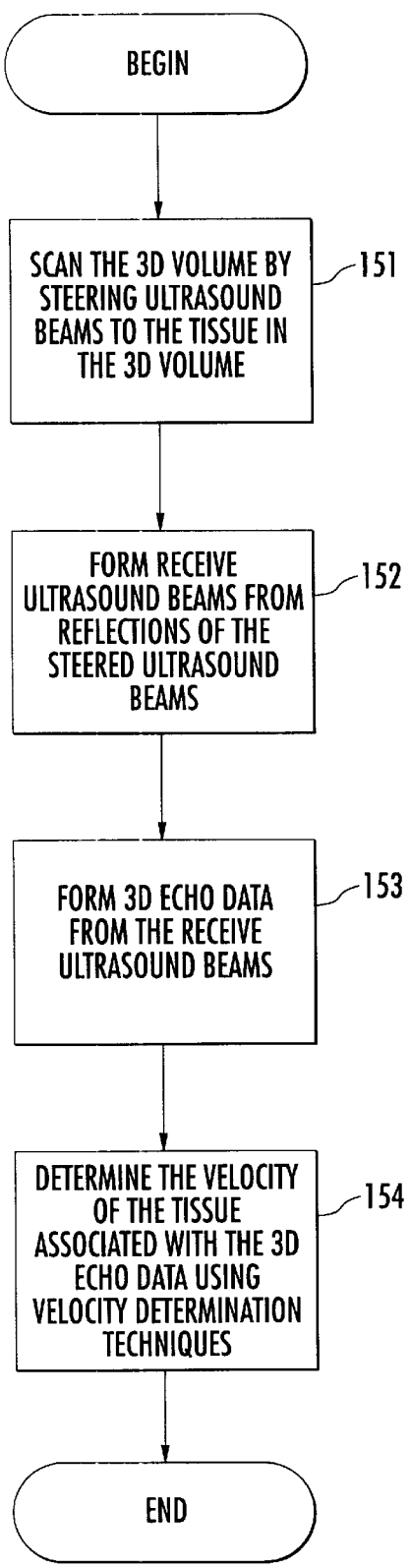
FIG. 1J is a flow chart that illustrates velocity determination operations according to the present invention.

FIG. 1J is a flowchart that illustrates operations of the present invention. According to FIG. 1J, the volumetric ultrasound system 105 determines the velocity of tissue in the 3D volume 100 by steering ultrasound beams to the tissue in the 3D volume 100 (block 151). Receive ultrasound beams are formed from reflections of the steered ultrasound beams from the tissue in the 3D volume 100 (block 152). 3D echo data is formed from the receive ultrasound beams (block 153), and the velocity of the tissue associated with the 3D echo data is determined using the velocity determination techniques described above (block 154). The velocity of the tissue can be displayed in real-time. For example, in one embodiment, a sub-volume of the 3D volume 100 can be scanned and the determined velocity of the tissue displayed in about 50 milliseconds (ms). The display of the tissue velocity can comprise a Color Flow Doppler (CF) display, a Pulse Wave Doppler (PW) display and/or a Continuous Wave Doppler (CW) display. In an alternate embodiment, the 3D echo data is used to create a Motion Mode (M mode) display, wherein the display represents the relative displacement of the tissue being scanned.

The 3D echo data is formed by steering ultrasound beams in an elevation direction and in an azimuth direction so that the steered ultrasound beams scan the 3D volume 100 as shown in FIG. 1A. The receive ultrasound beams are formed in the elevation direction and in the azimuth direction from the reflections of the steered ultrasound beams in the tissue. The formed receive ultrasound beams represent the echoes of the steered ultrasound beams from the tissue. Because the receive ultrasound beams are formed in the azimuth and elevation directions, the echo data represents echoes of the steered ultrasound beams in three dimensions. In a preferred embodiment of the present invention, the receive ultrasound beams are formed using receive mode parallel processing as discussed, for example, in U.S. Pat. No. 4,694,434 to von Ramm et al. entitled "Three-Dimensional Imaging System" which is commonly assigned to the present assignee and which is incorporated herein by reference.

In a 3D CF ultrasound system according to the present invention, the user may select a sub-volume 101 in the 3D volume 100 for investigation as shown in FIG. 1B. The volumetric ultrasound system 105 steers the steered ultrasound beams in the 3D volume 100 to cause the desired sub-volume 101 to be scanned. For example, the sub-volume 101 may be scanned twenty times to produce the 3D echo data for the CF display.

In PW and CW modes a beam of ultrasound energy is repeatedly transmitted in a single direction to obtain velocity information from a single depth or span of depths along the beam (PW Mode) or the sum of velocity information along the entire beam (CW Mode). In either mode, the transmit/receive line must be steered to the precise location of the tissue being investigated. Combining the steering with an echo image of the tissue allows for precise placement.

In PW mode a range gate also can be specified whose depth determines the center of measurement along the line and whose width determines the number of samples in depth to average to obtain an average gated velocity.

Aiming of the transmit/receive line and adjustment of the gate depth can be combined with accurate visualization of the targeted tissue through the adjustment of the section and the parallel slices.

Referring again to FIG. 1A, when the 3D echo data is formed, the user can select views of the data for display. For example, the user can select Constant mode (C) slices, such as first, second, and third C slices C1, C2, C3 that allow the user to view that portion of the 3D volume 100 which would be visible if the corresponding slice were removed from the 3D volume 100 for viewing. The 3D echo data used to represent the selected slice is retrieved and displayed. For example, if the 3D volume 100 contained a heart including a heart valve, the user could select a slice of the 3D echo data that passed through the heart valve and view the corresponding slice as if it were removed from the heart. Consequently, the presentation and examination of 3D objects may be more natural.

The first and second B slices B1, B2 are also selectable and allow the user to view that portion of the 3D volume 100 which would be visible if the corresponding B slice were removed from the 3D volume 100 for viewing. The 3D echo data used to represent the selected B slices is retrieved and displayed. According to FIG. 1A, the position of the first B slice B1 can be manipulated in the azimuth direction and the position of the second B slice B2 can be manipulated in the elevation direction. As the azimuth or elevation position of the respective B slice changes, the user is presented with new 3D echo data that corresponds to the changed position of the B slice. As described above, the 3D echo data corresponding to the selected B slice is retrieved and displayed. As shown in FIG. 1C, the first and second B slices B1, B2 intersect in the 3D volume 100 to define an intersection line 110. According to the present invention, the intersection line 110 can be used to aim the steered ultrasound beams along the intersection line 110. It will be understood that the aiming line can also be generated by selecting a point in a C slice.

The user steers the steered ultrasound beams in the 3D volume 100 by causing an aiming line to be displayed on at least one of the slices described above. For example, the user can use a trackball, a light pen, a tablet pen, a keyboard, or software or hardware switches or knobs to indicate the position of the aiming line on the first B slice B1. Accordingly, the volumetric ultrasound system 105 steers the steered ultrasound beams into the 3D volume 100 so that a portion of the 3D volume 100 that intersects the aiming line (a target) is scanned by the steered ultrasound beams. The 3D echo data corresponding to the target is processed to provide the velocity (for CF, PW, or CW) or movement (for M Mode) of the tissue.

FIG. 1C is a perspective view of the 3D volume 100 including first and second orthogonal B slices that define the aiming line. According to FIG. 1C, the aiming line 110 is defined by the intersection of the first and second orthogonal B slices B1, B2. For example, if the user chooses the aiming on the display of the first B slice B1, the position of the second B slice B2 in the 3D volume 100 is changed so that the new position of the second B slice in the 3D volume 100 intersects with the first B slice B1 to define the equation of the aiming line. Thereafter, when the user changes the aiming line 110 to investigate different tissue, the respective positions of the first and second B slices B1, B2 in the 3D volume 100 are changed so that the intersection of the first and second B slices define the new aiming line. Consequently, the aiming line is visible in both slices.

Figure 1K:
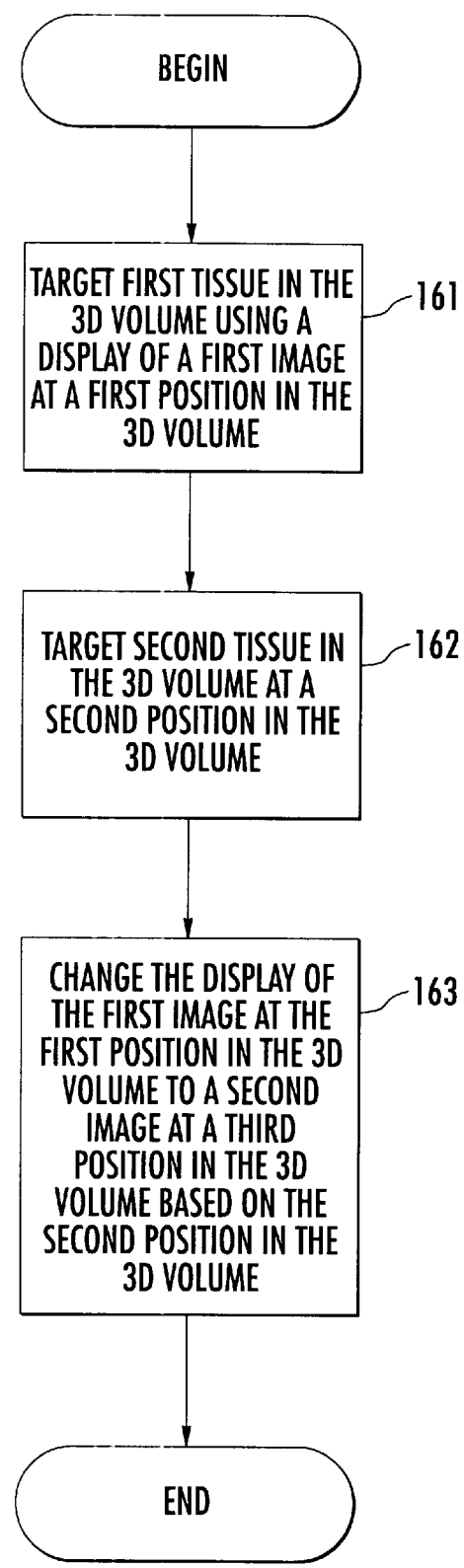
FIG. 1K is a flow chart that illustrates targeting of tissue according to the present invention.

FIG. 1K is a flowchart that illustrates operations of a volumetric ultrasound system according to the present invention. Operations begin in block 161, wherein first tissue in the 3D volume is targeted using a display of a first image at a first position in the 3D volume. Second tissue in the 3D volume is targeted at a second position in the 3D volume (block 162) and the display of the first image at the first position in the 3D volume is changed to a second image at a third position in the 3D volume based on the second position in the 3D volume (block 163).

FIGS. 1D–1G are views of B slices including first and second aiming lines 106, 107 used to steer the steered ultrasound beams to respective first and second target tissues 103, 104. According to the FIG. 1D, the aiming line 106 is generated on the display of the first B slice B1 to intersect with the first target tissue 103. According to FIG. 1E, the first aiming line 106 is generated on the display of the second B slice B2 to intersect the first target tissue 103.

As shown in FIG. 1F, the second aiming line 107 is generated on the display of the first B slice B1 to intersect with the second target tissue 103. For example, the user may wish to investigate the velocity of blood flow at a point that intersects the second aiming line 107, wherein the user may move the first aiming line 106 to the new position on the display of the first B slice B1 to define the second aiming line 107. When the second aiming line is generated on the display of the first B slice B1, the display of the second B slice B2 can be changed to display a third B slice B3, shown in FIG. 1G, which represents the B slice of the 3D volume 100 which intersects the first B slice B1 to define a new intersect line 110.

FIGS. 1H and 1I are untilted parallel views of the 3D volume 100 shown in FIG. 1C including respective indications of the first, second, and third B slices B1, B2, B3 shown in FIGS. 1D–1G. FIG. 1H shows the respective positions, in elevation and azimuth, of the first and second B slices B1, B2 in the 3D volume 100. The intersection of the first and second B slices B1, B2 defines a first point 120 that lies on the intersection line 110 that represents the first aiming line 106.

According to FIG. 1I, when the user generates the second aiming line 107, a second point 121 is determined, wherein the second point 121 lies on the second aiming line 107. The second aiming line 107 can be used to determine the respective positions of the first and third B slices B1, B3, in azimuth and elevation, in the 3D volume 100. When the respective positions of the first and third B slices B1, B3 are determined, the respective display the first and third B slices B1, B3 are changed to display the third and fourth B slices B3, B4.

It will be understood that the user may generate the second aiming line 107 that lies in the plane of the first or second B slices B1, B2, wherein either of the respective displays of the first or second B slices B1, B2 is changed. For example, if the second aiming line lines in the plane of the first B slice B1, the display of the second B slice B2 is changed. It will also be understood that the aiming line can be generated by use of a C slice, wherein the displays of the first and second B slices B1, B2 can be changed in response to the change in aiming line.

An equation of the aiming line is based on the equations of first and second planes that intersect the 3D volume 100, wherein the first and second planes include the first and second B slices B1, B2. In general, the intersection of the first and second B slices B1, B2 is determined by calculating the transformation matrix from the transducer coordinate system to the respective coordinate systems of the displays for the first and second B slices. An example solution to the transformation matrix is presented below.

Definitions

Coordinate systems: T=transducer, A=azimuth, E=elevation, and C=c-scan (or parallel).

Transformations: In general, the notation $M_{A\_B}$ denotes a 4×4 matrix which transforms points in B into A. For this system, we use the following transformations:

$$M_{T\_A} = \begin{pmatrix} a & 0 & 0 & -a*u_c \\ 0 & a*s & -a*c & -a*s*b \\ 0 & a*c & a*s & -a*c*b \\ 0 & 0 & 0 & 1 \end{pmatrix}$$

where a=pixels to samples scale factor, s=sin(az_tilt), c=cos(az_tilt), $u_c$=½ viewport width, and b=a vertical offset factor. The elevation matrix is similar:

$$M_{T\_E} = \begin{pmatrix} 0 & a*s & a*c & -a*s*b \\ a & 0 & 0 & -a*u_c \\ 0 & a*c & -a*s & -a*c*b \\ 0 & 0 & 0 & 1 \end{pmatrix}$$

The C-scan matrix involves two tilts (X and Y); sx=sin(x_tilt), cx=cos(x_tilt), sy=sin(y_tilt), and cy=cos(y_tilt). The depth of the center of the C-scan is denoted by $z_c$ and $v_c$=½ viewport height. The matrix is:

$$M_{T\_A} = \begin{pmatrix} a*cx & 0 & -a*sx & -a*cx*u_c \\ -a*sx*sy & a*cy & -a*cx*sy & -a*(-sx*sy*u_c + cy*v_c) \\ a*sx*cy & a*sy & a*cx*cy & -a*(sx*cy*u_c + sy*v_c) + z_c \\ 0 & 0 & 0 & 1 \end{pmatrix}$$

Sector-sector Intersections

Intersections between the azimuth and elevation sectors are used to define the M-mode and spectral aiming lines, colorflow boundary lines, b-volume measurement (helps to define the boundaries of the object being measured), and for general navigation (understanding the relative positions of az and el wrt each other).

One method for deriving the intersection between the az and el sectors is to use the transformations that define their coordinate systems (CSs) relative to the transducer to derive the intersection line. Specifically, the intersection line in the azimuth sector can be derived as follows.

Since the coordinate systems are defined such that the X-Y plane of each one is the plane of the sector, the intersection between the X-Y planes of the two coordinate systems gives the intersection line. To find this intersection, we begin with the transformation matrices defining each coordinate system.

Given $M_{T\_A}$ and $M_{T\_E}$, we can express E in A via the following transformation:

$$M_{A\_E} = M_{A\_T} * M_{T\_E} \text{ (where } M_{A\_T} = (M_{T\_A})^{-1})$$

The third column of $M_{A\_E}$ gives the Z axis of E expressed in the A coordinate system. But this is just the normal to E's X-Y plane. The normal to A's X-Y plane is just its Z axis, which is always [0, 0, 1] in the A CS. The cross product of these two vectors gives the direction for the intersection line:

$$V_{int} = V_Z \otimes V_{A\_EZ}$$

The two plane equations are: Z=0 (Az's X-Y plane) and Ax+By+Cz+D=0 (El's X-Y plane in A), but since Z=0, the latter reduces to: Ax+By+D=0. A and B are just the x and y components of $V_{int}$, and $D = -(Ax_{A\_E} + By_{A\_E} + Cz_{A\_E})$, where $x_{A\_E}$, $y_{A\_E}$, and $z_{A\_E}$ are the first three elements of the fourth column of $M_{A\_E}$ (these are the translation offsets that express E's origin in A). Since this vector is in the X-Y plane of E, it can be used to define that plane. Setting Z=0 in the equation of E's plane gives the line of intersection in A. An analogous process can be used to find the intersection of A in E.

Sector-parallel Intersections

Sector-parallel intersections are used to draw the bounding box in the parallel viewport for the CF image, to draw the aiming markers in the parallel viewport for the PW, CW and M modes and to provide general information on the location of where the sectors intersect the parallel viewports.

Sector-parallel intersections can be computed in the same way as is done for the sector-sector intersections, but using the transformation matrix for the parallel viewport instead.

Viewport Point to Transducer Transformation

Transformation from viewport to transducer space can be used to select an aiming line and depth in PW mode, and aiming line in CW and M modes, and the aiming and depth in CF modes through the use of a pen or other screen pointing device.

This transformation is also used for determining the distance between two points in the volume. The user selects one point in any viewport and a second point in the same or any other viewport. Each point is transformed into the transducer CS and the distance between them can be directly calculated.

To get the location in 3D of a point selected in a viewport, the point in viewport is transformed by the appropriate viewport-to-transducer matrix:

$$V_{T\_P} = M_{T\_A} * V_{A\_P}$$

which gives the point's location in transducer space.

Correction Line

Use 'S' to denote the sector coordinate system (A or E). PB=bottom point of intersection line (where it hits the bottom of the sector); PT=the top point. Use capital V to denote a regular 3-vector, capital U to denote a unit vector; small u and v denote viewport coordinates in pixels.

The calculation can be performed as described below. Add the negated correction angle to the aiming angle and compute the corrected aiming vector in each sector coordinate system:

$$V_{aim} = V_{S\_PB} - V_{S\_PT}.$$

Compute the normal for the plane defined as perpendicular to the sector and through the rotated line for each sector:

$$U_{aim} = V_{aim} / \|V_{aim}\|$$

$$\tan(A_{aim}) = \frac{u_{S\_PB} - u_{S\_PT}}{v_{S\_PB} - v_{S\_PT}}$$

$$A_{net} = A_{aim} - A_{cor}$$

$$U_{cor} = (\sin(A_{net}), \cos(A_{net}))$$

$$U_{norm} = (\cos(A_{net}), -\sin(A_{net})).$$

Rotate normals and aiming line into the transducer coordinate system.

$$U_{T\_aim} = R_{T\_S} * U_{aim}$$

$$U_{T\_norm} = R_{T\_S} * U_{norm} \text{ (for az and el)}$$

Take the cross products of the normals to obtain the intersection vector.

$$U_{int}=U_{T\_norm\_az} \otimes U_{T\_norm\_el}.$$

Take the dot product of the intersection vector and the aiming vector to get the cosine of the correction angle.

$$\cos(\alpha)=U_{int} \cdot U_{T\_aim}.$$

In PW mode a range gate also must be specified to indicate the range over which velocity data is presented to the user. For example, the user may specify a depth range for which the velocity data is displayed. The velocity data not falling within the specified range is not displayed. In one embodiment, the C slices are used to specify the range gate and is shown perpendicular to the aiming line. To display the range gate, the present invention determines the equation of the line perpendicular to the aiming line at the range gate depth in the plane of the B slice in which the range gate is shown.

The user selects a position in the ultrasound scan data that corresponds to the located tissue using the tissue location in the first direction and the tissue location in the second direction and directing a Doppler beam to the selected position in the ultrasound scan data. The combination of locating the tissue in the first and second directions allows the user to locate the optimal aiming position for measuring the velocity of the tissue. Directing the Doppler beam to the optimal location in the tissue may allow a more accurate estimation of the tissue velocity.

The array 12 also periodically scans the 3D volume 100 to provide an updated image of the 3D volume 100 to indicate the accuracy of the aiming line with respect to the tissue under investigation. The user may thereby adjust the direction of the aiming line to maintain an accurate velocity estimate.

There are a number of advantages that can be obtained by 3D aiming of PW and CW measurements. A user can visualize the complete structure to be measured even if it was not in line with the aiming of a single sector from the transducer. For example, if a user wished to take measurements across a valve, he could place the valve in a parallel view then steer across the face. The volumetric measurement allows the user to steer around a target area while reducing the probability that a peak velocity will be overlooked because it was outside of the 2 dimensional sector.

Another factor in the PW measurement is the correction angle. Because the PW mode measures velocity in the direction of the transducer, if the flow is at an angle to the aiming line, a lower velocity will be measured. In particular:

$$Vm=Va*\cos(\alpha)$$

Where Vm=Measured velocity

Va=Actual velocity

α=Correction angle.

With a volume echo image, the user can make a more precise determination of the direction of flow to set the correction angle. In the present invention, the correction angle is indicated to the user by lines on the two sector scans. These can be set by soft or hard buttons or by a trackball, mouse or pen. Once the correction angle is selected, the calculation for determining the absolute correction angle from the angles in the two sectors and drawing the lines in the sectors is involved. The calculation can be performed as described below.

Add the negated correction angle to the aiming angle and compute the corrected aiming vector in each sector coordinate system. Compute the normal for the plane defined as perpendicular to the sector and through the rotated line for each sector. Rotate normals and aiming line into the transducer coordinate system. Take the cross products of the normals to obtain the intersection vector. Take the dot product of the intersection vector and the aiming vector to get the cosine of the correction angle.

The present invention averages the velocity data across a range gate. Since for a given transmit line, 16 receive lines occur providing a volume of data, the system can average not only in depth but also across a limited span. This allows a user to define a complete volume over which the velocity is made. In other words, the velocity measurement is not limited to a ray from the transducer. By transmitting two or more lines, a larger volume can be defined.

Color Flow Mode

Management of Color Flow (CF) mode includes controlling the hardware to maintain the highest possible frame rate, allowing the user to steer the volume in which the CF image will be measured, indicating the selected volume to the user, and providing measurement.

CF measurements involve repeated transmits in the same direction. These transmits may be grouped together in time or they may be separated at intervals. If they are separated, other transmit lines may be included in the delay spaces.

In 3D the safety issues can complicate this process. When two transmit lines are close in space, they may add to the heating of the tissue. In conventional 2D systems, heating occurs from the adjacent lines in the 2D sector, but in 3D there can be more adjacent lines. According, the user may be limited in both the azimuth and elevation spans to insure the heating of a single area of tissue is not too great.

Avoiding overheating can be accounted for by multiplying a correction factor to the CF portion of the Ispta.3 safety calculation. One example of such a correction factor for the current implementation is as follows:

$$\text{CorrFactor}=0.9-0.9*\exp((1-N)/12.8)+N/2560$$

Where N=Number of transmit lines in a frame.

The minimum azimuth and elevation span for the color flow is also determined based on empirical measurements for each type of transducer. Aiming of the CF volume is different for 3D than for 2D. In conventional ultrasound, movement of the trackball in x would steer the CF aim while movement in y would adjust the depth. In the current invention, because there are more degrees of freedom, the trackball could be used to control steering as follows:

| Trackball State | X Movement | Y Movement |
| --- | --- | --- |
| CF Steering | Azimuth Aim Steering | Elevation Aim Steering |
| CF Span | Azimuth Span Adjustment | Elevation Span Adjustment |
| CF Depth | Depth Span Adjustment | Max Depth Adjustment |

Trackball state is changed by pressing a switch near the trackball. The steering could also be accomplished by soft or hard controls. The controls also can be grouped to combine aim and depth or aim and span for each mode. Other combinations also are possible.

Feedback to the user of the aimed position is accomplished by showing lines on the echo image in sector and parallel views. In the sector views, lines are drawn on both edges with an indication of the top and bottom. Calculations for these lines are analogous to those for sector-sector intersections used in PW mode. Lines on the edges can also be drawn in the parallel view.

In another aspect of CF steering according to the present invention, the echo image can be steered outside of the CF volume. Since the CF volume is a sub-volume of the echo image and the echo sector and parallel views can be steered throughout the volume, the user needs the aiming lines to disappear in a given view when that view no longer contains any color flow data. This provides clear indication whether there is no CF data because of steering or because there is no flow. This could also be accomplished by limiting echo steering to the CF region of data.

CF measurements in 3D allow for the measurement of the volume of a region over which a flow exists. Making a series of measurements as sectors are tilted or as the parallel depth is changed can define a volume and allow calculation of the enclosed space. The resulting calculation can provide a value for the amount of fluid flowing in a given time frame. Measurements can further be taken over a period of time to determine the total volume of fluid that has flowed across a given region. This can be used to quantify the precise severity of a leaky cardiac valve, for example.

The complete volume of CF velocity, variance, and power information is stored in memory and can be transferred to or loaded from a removable storage media such as an optical disk. This allows subsequent review of any slice of data within the CF volume at a later time.

M Mode

Aiming and steering of M Mode is analogous to that of PW mode without the range gate. In M Mode, a scrolling display of the echo data on the given aiming line is displayed. As in PW mode an aiming line is shown in the sector and parallel views. The sector views are tilted to show the echo data that contains the aiming line. The parallel views also can have a marker which indicates where the aiming line passes through.

Because a single transmit results in 16 receive lines, 3D M Mode has the unique capability to allow some slight steering from the vertical. With the current invention, this could be done in post processing as a line is calculated determining the depth sample to use from each line. By transmitting two or more lines, further steering could be accomplished at the cost of slower sweep speed.

Figure 2:
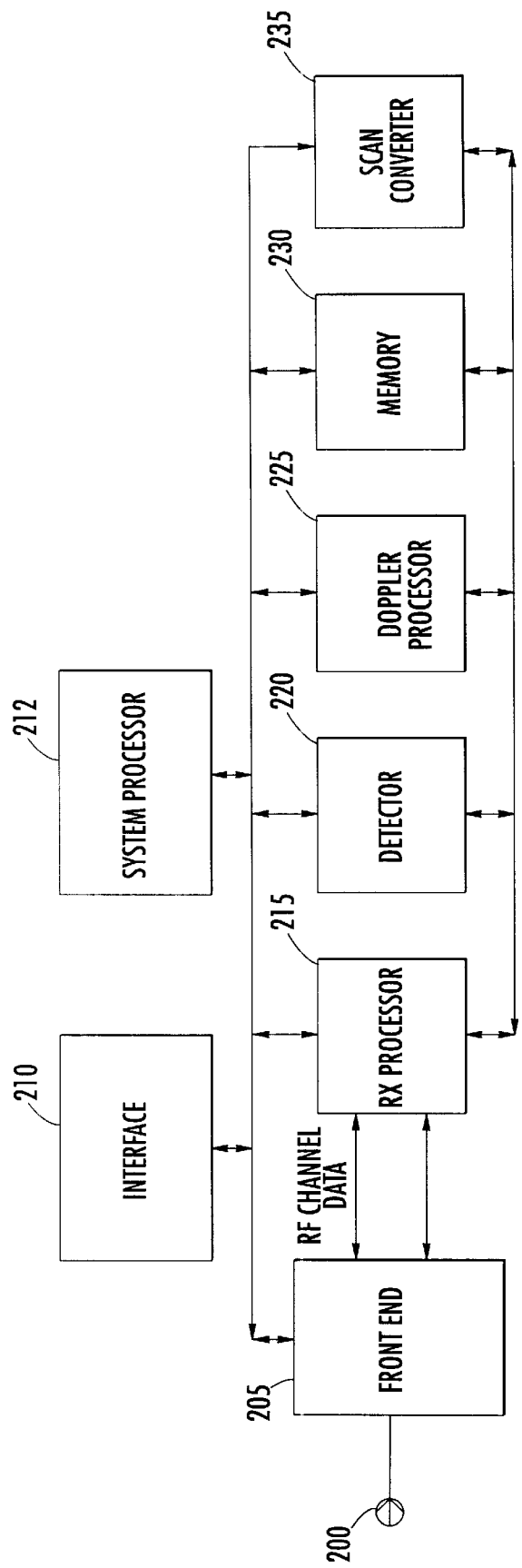
FIGS. 2 and 3A are block diagrams of volumetric ultrasound systems according to the present invention.

FIG. 2 illustrates a 3D volumetric ultrasound imaging system according to the present invention. A transducer 200, including the array 12, generates the steered ultrasound beams and receives echoes created by the steered ultrasound beams propagating through the 3D volume 100 under the control of a front end 205. In particular, the transducer 200 transmits ultrasound energy to produce the steered ultrasound beams for a first period and receives for a second period. For example, the transducer 200 may transmit ultrasound energy for several microseconds and then receive the echoes of the transmitted ultrasound energy. The transmitting time is determined by the phasing of the transducer 200. The receiving time is determined by the depth of the tissue in the 3D volume 100.

An interface 210 provides input to the system processor 212 via user input. For example, the user can select the positions of the B slices in the 3D volume 100 via the interface 210. A system processor 212 accepts input from the interface 210 and coordinates the operation of the components described herein. For example, the system processor 212 can run a computer program that controls the format of the information displayed in response to the user input via the interface 210.

The front end 205 controls the transducer 200 and conditions the ultrasound scan data received by the transducer 200 for use by the system. The front end 205 produces radio frequency (RF) channel data that corresponds to the ultrasound scan data received by the transducer 200.

An RX processor 215 controls the phasing of the signals received from the transmission of ultrasound energy. The phasing of the received signals generates 16 parallel receive ultrasound beams to measure the ultrasound energy reflected from a particular position.

A detector 220 filters the 16 parallel receive ultrasound beams received from the RX processor 215. The output of the detector 220 is then provided to the Doppler processor 225. Alternately, the output of the detector 220 is provided to the memory 230.

A Doppler processor 225 receives the filtered data from the detector 225 and generates Doppler data corresponding to the selected position in the ultrasound scan data. The Doppler processor 225 determines the phase shift in the ultrasound energy reflected from a located object in the ultrasound scan data and thereby determines the velocity of the tissue at the selected position. The Doppler processor 225 can generate spectral Doppler data (PW data or CW data) or color flow Doppler data from the filtered data. Both techniques are used to analyze the movement of tissue (such as blood flow) in the 3D volume 100.

A memory 230 stores the output of the detector 220 or the Doppler processor 225. The stored data is accessed by the system processor 212 in response to user input. For example, when the user selects the desired B slices via the system processor 212 of the scanned ultrasound data, the ultrasound data stored in the memory 230 is accessed to provide the desired image to the user.

Blood flowing in a vessel will show different velocities in the center of the vessel and at its outer diameter. Typically, the velocity will be highest in the center and less towards the outer diameter (it may almost reach zero close to the vessel walls). All of the blood is moving in the same direction, thereby generating a so-called laminar flow. The flow will, however, be disturbed by alterations in blood vessels such as arterial plaque or a stenosis.

To display and evaluate the flow profile in a vessel, the Doppler processor 225 uses a method called spectral analysis. The reflected ultrasound signal is evaluated for the frequencies present, representing the velocities of blood flow in a vessel. The Doppler processor 225 separates the detected frequencies into ranges of equal sizes. For each frequency range, the intensity is calculated, the intensity representing the amount of blood flowing at a certain speed.

The result of these calculations is a display of the spectral distribution of blood flow, lighter shades meaning higher intensities of blood flow, darker shades meaning higher intensities. The intensities are plotted along the vertical frequency axis. Thus, the whiter dots on the display represents the intensity of a certain frequency or velocity. The spectral data may then be plotted on a horizontal time axis and scrolled to show the variation in the blood flow over time.

Color Doppler mode depicts, in real time, an image related to the tissue movement in the 3D volume 100 (such as blood flow in vessels). The filtered data is processed by the Doppler processor 225 to determine the velocity of a tissue on which a particular scan line of the ultrasound scan impacts and is reflected. Ranges of velocities are assigned colors by the Doppler processor 225. The determined velocities are then mapped to the color that corresponds to the velocity range in which the determine velocity falls. For example, positive velocity data may be assigned blue and negative velocity data may be assigned red. The Doppler data (spectral or color) is then transmitted to the scan converter for display.

The Doppler processor 225 will now be described in greater detail with reference to FIGS. 3A–8.

Doppler Processor

This section describes the Doppler Processor 225 used to process the volume data provided from the Detector 220 and its input chain of the Rx Processor 215, Front End 205 and Transducer 200. This data is from a selected ray in the tissue as determined by the directed Doppler transmit beam located from the viewpoint of two directions within the ultrasound region.

The following terms are defined for use in this section as follows;

Color Flow: This refers to the processing and resulting display of an image, which utilizes color to represent velocity values at the various image points. Variance information is also included by the addition of another color. The specific sequence of colors and their intensities are usually defined by a color table setup by the controlling software.

Power Doppler: This refers to the power processing and resulting display of an image which utilizes color to represent power values at the image points. The specific sequence of colors and their intensities are usually defined by a color table setup by the controlling software.

Spectral Doppler: This refers to the processing and resulting linear display of frequency spectral data as a function of time scrolling across the display. The y-axis usually represents +/–frequency or velocity, and the x-axis represents time. Brightness at a specific point usually represents signal strength at that particular frequency and time.

Packet: Packet refers to the basic data set at a particular depth that is used in Color Flow processing, i.e. input as a set into the wall filter processing function, including outliers and inner values at the respective depth. The inner values within the packet are defined as the Inner Packet described below.

Inner Packet: Inner Packet refers to the samples within the packet which are used directly for calculating velocity, variance, power, and magnitude. The Inner Packet size used herein is always equal to the Packet size minus 2.

Ensemble: Ensemble refers to the basic data set at a particular depth that is used as input to Spectral Doppler processing, i.e. this is analogous to the term packet which is used in color flow.

Kernel: Kernel refers to the basic set of processing elements (Field Programmable Gate Arrays—FPGAs) and random access memory (RAM) which process one of the 16 RF Sums streams of incoming data. One each of the Wall Filter and Velocity/Power FPGAs, along with one 128K×32 RAM chip comprise the major functional entities within a Kernel.

Doppler Processor Functional Overview

The Doppler Processor 225 is provided input directly from the Digital Detector Board 220. The Digital Detector Board 220 is provided analog data input from the Rx Processor 215 which is fed by the Front End 205 and Transducer 200. These are represented on the functional diagram shown in FIG. 3A.

Figure 3A:
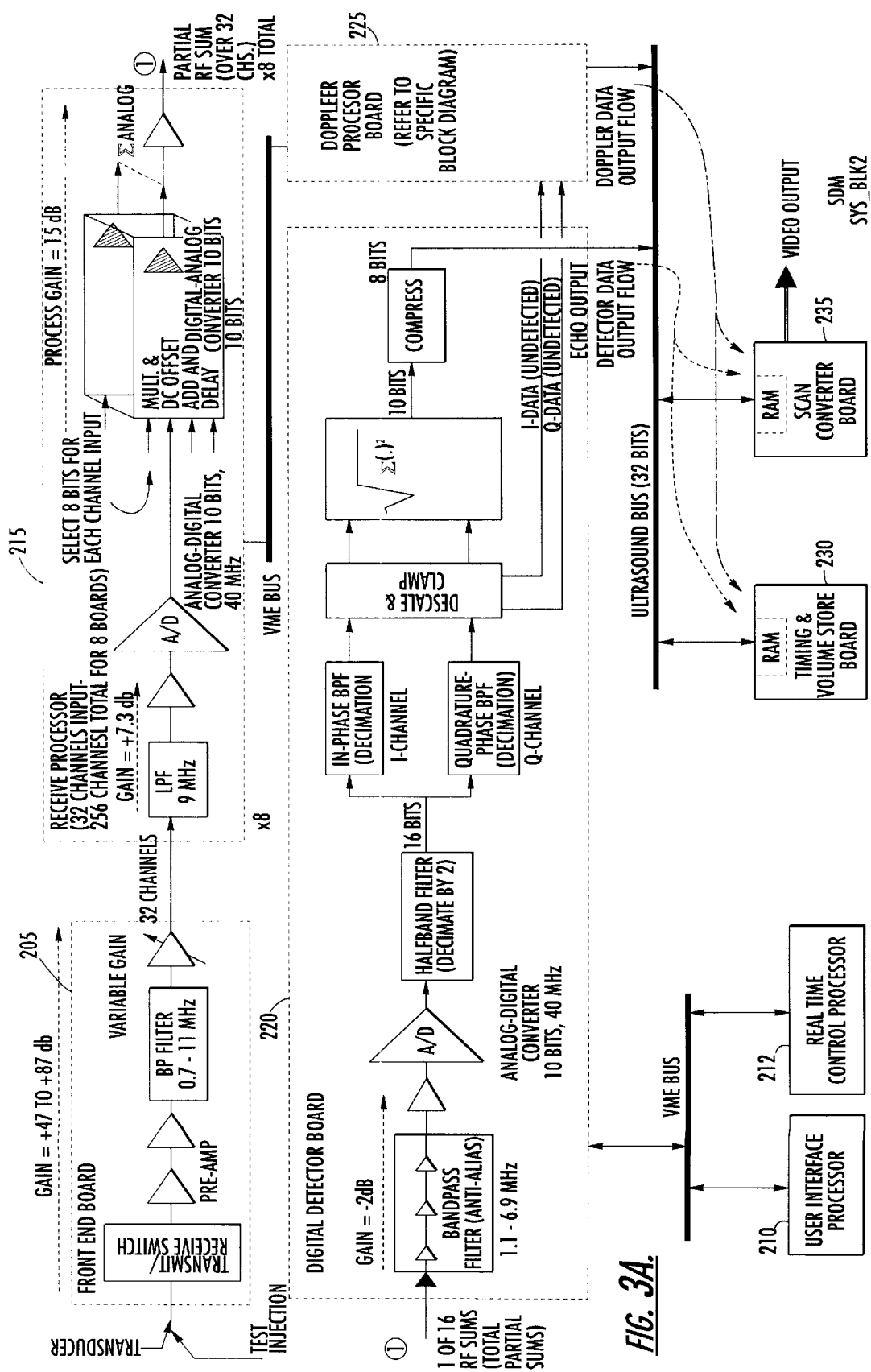
Figure 3B:
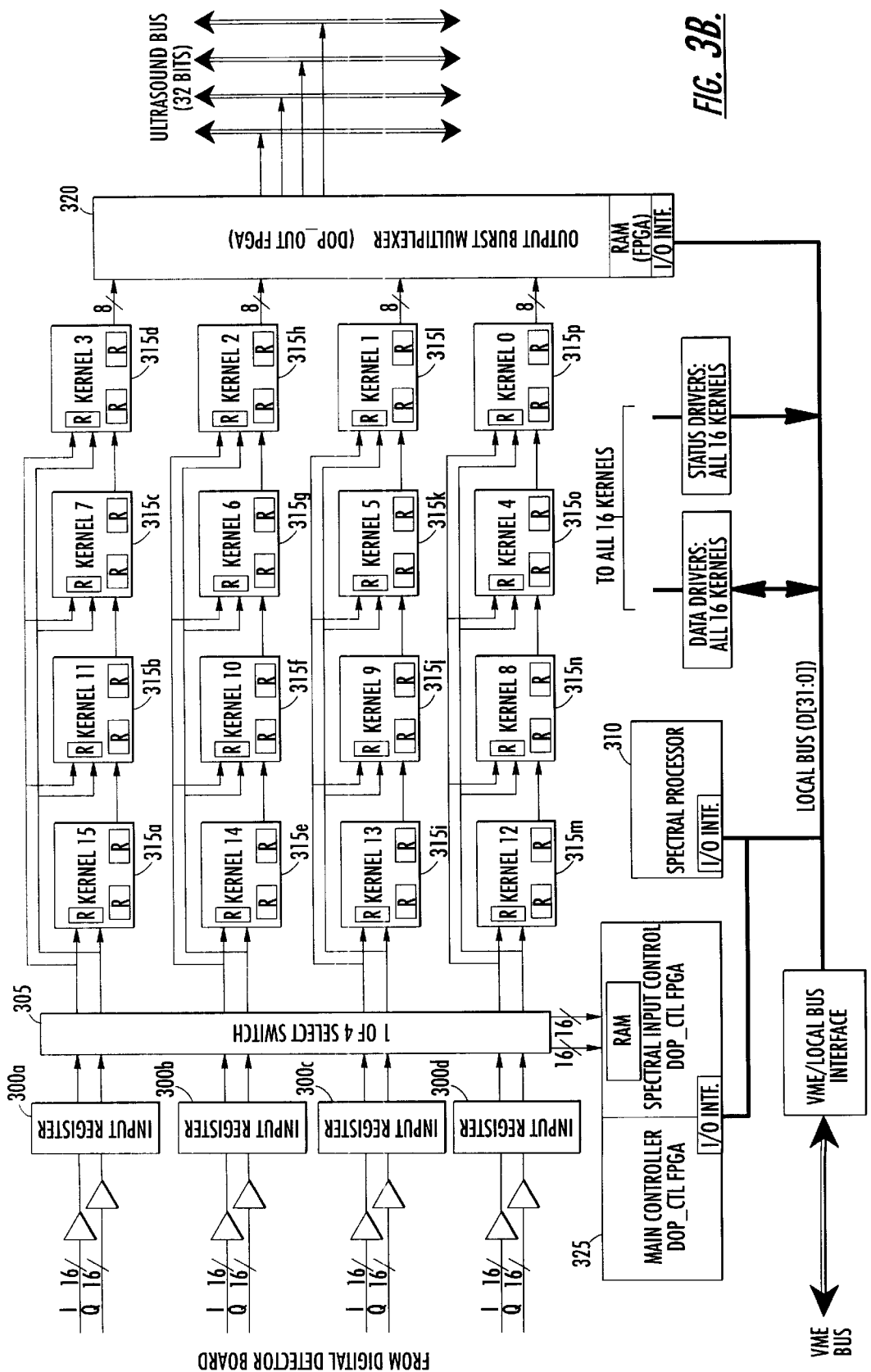
FIG. 3B is a block diagram of an embodiment of the doppler processor shown in FIG. 2.

A functional block diagram of the Doppler processor 225 is shown in FIG. 3B. According to FIG. 3, the Doppler processor 225 receives 16 RF Sums of in-phase (I) and quadrature-phase (Q) data sample pairs from the Detector (DDT) 220. The Doppler processor 225 is designed to receive up to 512 I and Q sample pairs total per RF Sum for each receive line. This data is output from the I and Q Bandpass digital filters on the DDT 220, after the normal decimation and descaling operations have been performed, and is registered upon input to the Doppler processor 225. The data is input to the Doppler processor 225 as 4 pairs of I and Q 16 bit values, yielding 128 data bits simultaneously in 2's complement. Thus, the total of 128 bits are input as 4 sequential bursts to yield 16 RF Sums of I and Q data pairs.

Figure 4:
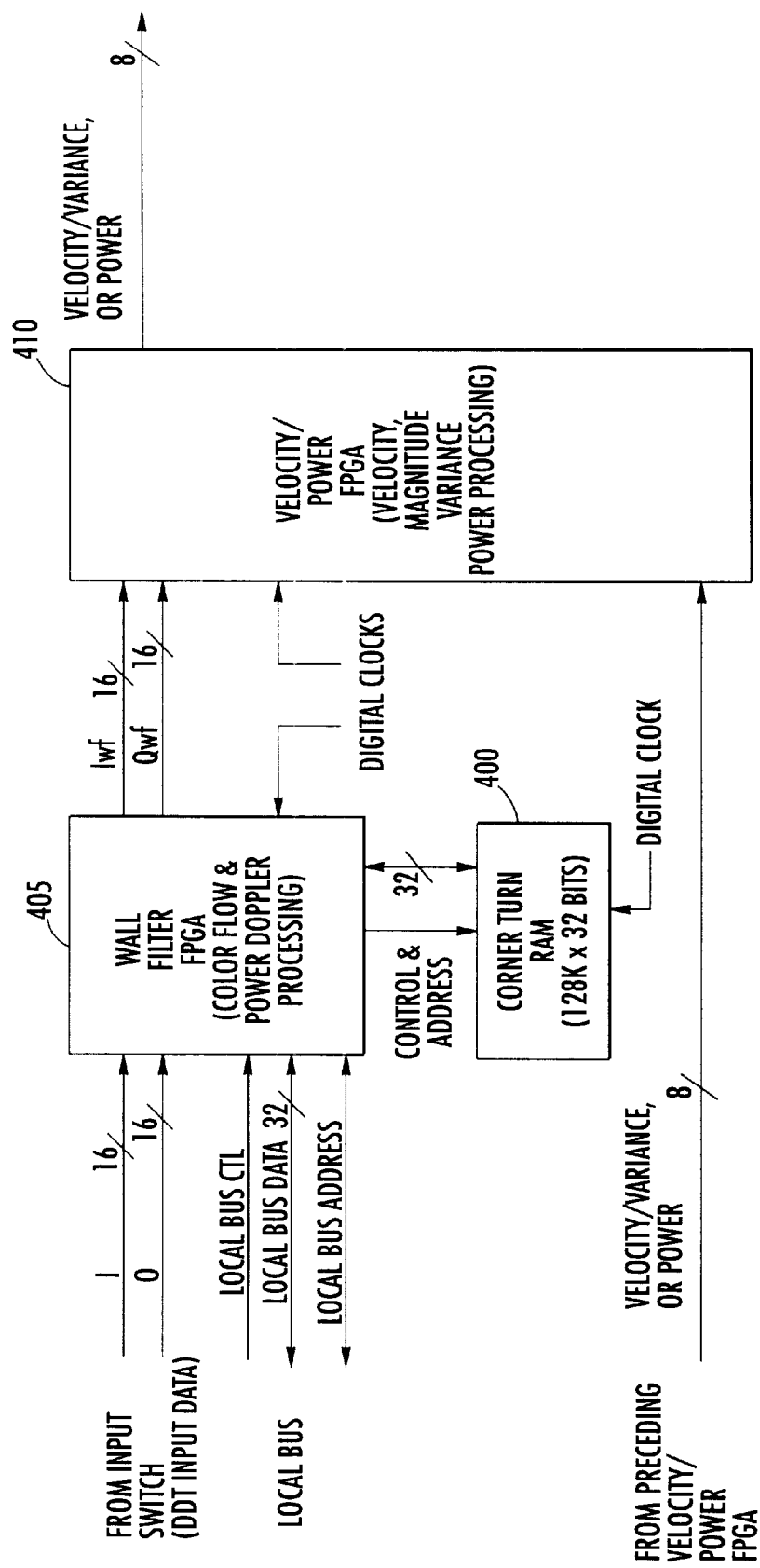
FIG. 4 is a block diagram of an embodiment of an RF SUM processing kernel according to the present invention.

In the Color Flow or Power Doppler Modes, the I and Q values are simultaneously provided in parallel to 4 RF Sum processing modules or kernels at once, with 4 phases to supply I and Q data to each of the 16 kernels. A block diagram of the RF Sum processing kernel is shown in FIG. 4. For each kernel, I and Q samples are initially stored in the Wall Filter FPGA memory for later bursting into the Corner-Turn Random Access Memory (RAM) 400.

The Corner-Turn RAM 400 is organized as multiple (up to 16) windows, each window is able to contain up to 512 samples for each of a maximum of 16 lines, i.e. up to 8K×32 bit words per window, or 128 K×32 bit words total for each kernel. This memory capacity supports line interleaving for the line receiving scheme shown in FIG. 5, i.e. outlier lines separated by one or more windows on either side of the inner lines. Note that spreading the outliers further apart results in reducing the interleaving choices.

Figure 5:
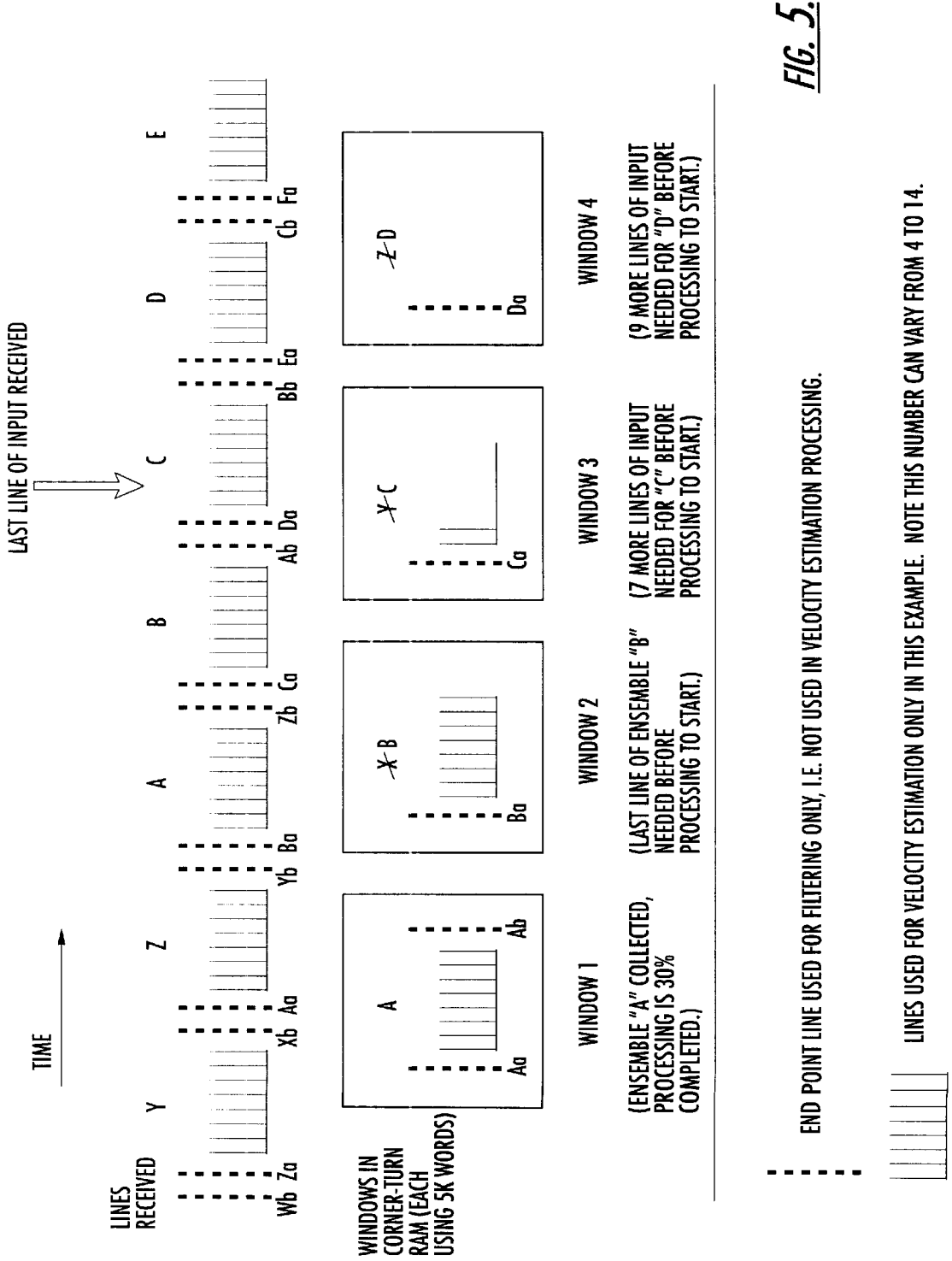
FIG. 5 illustrates exemplary receiving of single interleaved line data for temporary storage.

FIG. 5 demonstrates an example of receiving single interleaved line data for temporary storage in the Corner Turn RAM 400 prior to wall filtering. The I and Q samples, are burst written into one of 4 current windows in the Corner-Turn RAM 400, i.e only 4 windows are needed. Each window will accumulate a packet of lines (up to 16) for processing. The input line is commanded to be placed in a specific line position in the window by the System Control Processor. The data within a window in the Corner-Turn RAM is subsequently read by the Wall Filter 405 FPGA within each kernel to begin processing. The reads begin at the start depth pointer and continue for the commanded length. This starting pointer value and number of depth samples is setup by the User Interface Control Processor.

Within each kernel, filtered I and Q data samples are then passed to the Velocity/Power FPGA 410 where processing is performed over the packet of lines within the window. Subsequently, the Velocity/Power FPGA 410 for each kernel provides output of the velocity values along with variance, and power. Power is currently used for all display thresholding by a subsequent processing function external to the Doppler processor 225. This output data is provided to the Ultrasound Bus, 4 RF Sums at a time, in the same order as the RF Sum data was previously input to the Doppler processor 225 and provided to each kernel. Velocity and power (threshold) output data are provided for each depth value initially loaded from the DDT 220.

In the Spectral Doppler Mode, the I and Q values are received as described above into the 128-bit wide input register. However, one or more of the 16 input RF Sums is selected by the Select Switch for passing to the Spectral Processor which performs Fast Fourier Transforms (FFT) on the data. The Spectral Processor transfers data over the Local Bus as indicated in FIG. 3B. The Spectral Processor accumulates I and Q data in its local Corner-Turn RAM from the selected RF Sum, and performs wall filtering as needed, followed by an FFT computed over an ensemble of lines contained in the window selected. Preceding the FFT computation, averaging of I and Q samples over the range gate and span is accomplished.

The following section describes the functions performed by the Doppler processor 225 in FIG. 3B.

Input Registers and Select Switches

Figure 6:
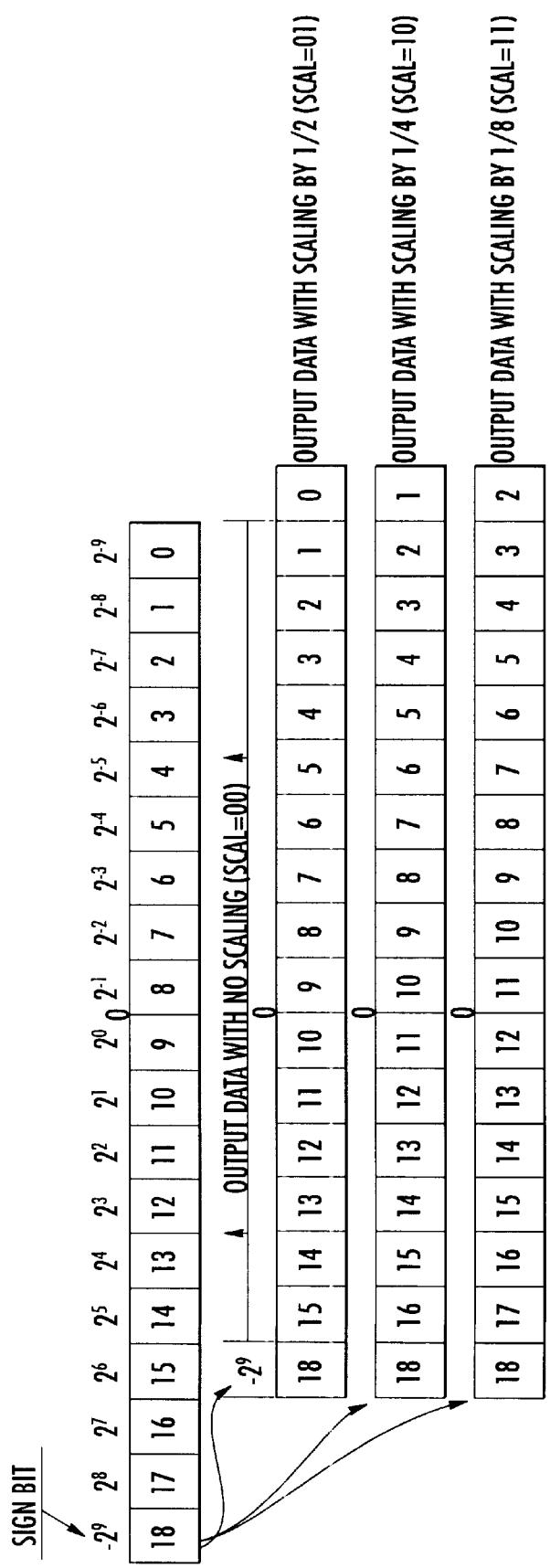
FIG. 6 is a diagram of an embodiment of input registers on the doppler processor shown in FIG. 2.

According to FIG. 3B, Input Registers 300a–d temporarily store the 4 pairs of I and Q input values (128 data bits)

from the Detector 220. The registered input can then be provided to either the RF Sum Processing Kernels 315a–315p or the Spectral Processor 310 via the Select Switches 305. The data format as received from the Detector 220 is as shown in FIG. 6. Note that in the "No Scale" format, the least significant bit 0 corresponds to the least significant bit output from the I and Q filters on the DDT 220. This bit 0 is dropped by the DDT 220 in the "½ Scaled" format, as are succeeding bits in the other two "Scaled" formats. The decimal point is between bits 9 and 10 in ½ scale, 10 and 11 in ¼ scale, and 11 and 12 in ⅛ scale.

RF Sum Processing Kernels (Modules)

The 16 RF Sum Processing Kernels 315a–p perform the processing for Color Flow and Power Doppler processing. Each kernel consists of the Wall Filter FPGA 405, local Corner-Turn Memory 400, and the Velocity/Power FPGA 460 shown in FIG. 4.

The following describes the data movement through the kernels. The I and Q pairs pass through the Input Select Switches and are latched directly into the respective RF Sum processing kernel 315a–p. Four RF Sum processing kernels are connected together on an input bus for synchronously receiving their respective I and Q data, e.g. RF Sums 0, 4, 8 and 12 are bussed together, etc. The particular kernel registers its data in a time division manner one line at a time, and accumulates the desired number of line packets including the outlier end points for wall filtering. Once an entire window (multiple packets) has been received per RF Sum, the wall filtering processing can be completed with subsequent data transfer to the Velocity/Power FPGA. The filtered results of the central values within the I and Q packets are transferred to the Velocity/Power FPGA 410. The Velocity/Power FPGA 410 performs the velocity and power calculations, and computes the variance along with the magnitude of the velocity vector. The output values are temporarily stored within the output section of each Velocity/Power FPGA 410 until they are synchronously transferred (under control of the Output FPGA within the Output Burst Multiplexer 320) to the Ultrasound Bus. Note that the Output FPGA synchronizes all 16 kernels for output, and that velocity/variance data and power data is provided by each kernel. The Color Flow mode enables velocity/variance data with threshold (power) data to be available for output. Power mode enables power data (replaces velocity/variance data) and threshold (also power) data to be available for output.

RF Sum Processing: Wall Filtering

Color flow or Power Doppler wall filtering is performed for each RF Sum kernel 315a–p in the respective Wall Filter FPGA 405. The wall filtering process depends upon the packet size established by the Doppler Control Register. The process operates over the accumulated packet data in the Corner-Turn Memory 400, and provides the processed filtered data directly to the Velocity/Power FPGA 410. The wall filtering algorithm is provided in the Processing section below. The output of each Wall Filter FPGA 405 is provided as a stream of filtered data associated with each incoming packet processed. The number of values in each set is two less than the packet size.

RF Sum Processing: Corner-Turn Memory

Each RF Sum processing kernel contains 128 k×32 bits of Corner-Turn memory 400. This memory is written by its respective Wall Filter FPGA 405 one line of data at a time. The Wall Filter FPGA 405 reads the data out for wall filter processing one depth at a time.

RF Sum Processing: Velocity, Variance, Magnitude, and Power Processing

In Color Flow mode, velocity/variance and power (threshold data) are provided as output. In Power mode, power data is provided as output with power data also available as threshold data.

The velocity and variance output values for a single RF Sum kernel are provided as a stream of single bytes, and are temporarily stored in the respective Velocity/Power FPGA 410 memories (16) for subsequent transfer to the Ultrasound Bus.

The power output values for each RF Sum module are provided in single bytes, and are temporarily stored in the respective Velocity/Power FPGA 410 memories(16) for subsequent transfer to the Ultrasound Bus.

Spectral Processing

Figure 7:
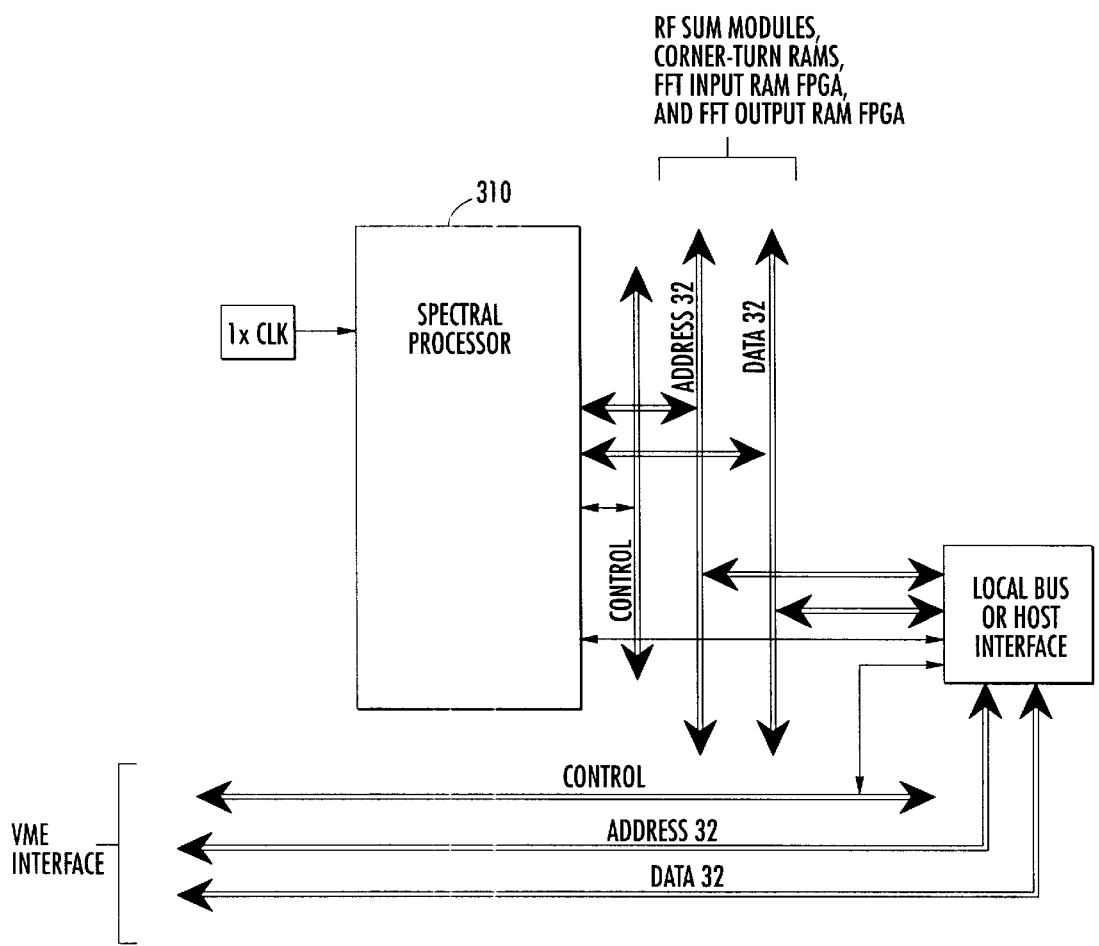
FIG. 7 is a block diagram of an embodiment of a spectral processor according to the present invention.

The Spectral Processor 310 performs the Spectral Doppler Fast Fourier Transform (FFT) processing. FIG. 7 shows its functional block diagram. One or more of the RF Sums data stream is transferred to the input memory of the Doppler Controller FPGA 325. The Spectral Processor 310 transfers the input data from the Doppler Controller FPGA to its internal memory in response to an interrupt from the Doppler Controller FPGA 325. This interrupt occurs when the pre-determined number of depth values have been received and stored in the Doppler Controller FPGA 325.

The input values are accumulated in the Spectral Processor 310 memory as directed under software control via the input window and line selection in the Doppler Control Register. In general the Spectral Processor 310 performs wall filtering, followed by averaging samples over the range gate and span, and then performing the FFT over the accumulated ensemble of lines. The computed spectrum's peak value is also determined. The spectrum and peak data are temporarily stored in the Output Burst Multiplexer FPGA 320 internal memory before transfer over the Ultrasound Bus.

Doppler Controller

Software controls the Doppler Controller FPGA 325 by writes to the Doppler Control Register. The Doppler Controller places the board in the commanded mode and provides sequencing signals to the related lower level controllers and processing elements within the kernels and the Doppler Output FPGA 320. The Doppler Controller FPGA 325 also provides the control interface for receiving the input data from the Detector 220, and directing it to the kernels for Color Flow processing Additionally, the Doppler Controller 325 serves as the FPGA for controlling and providing temporary input buffer memory for subsequent spectral data processing. It selects the RF Sum stream of data as directed, buffers the samples, and interrupts the Spectral Processor 310 once per receive line after the proper number (range gate) line samples are received. The Spectral Processor may read the data from the Doppler Controller 325 internal memory to begin spectral processing.

Output Burst Multiplexer

Figure 8:
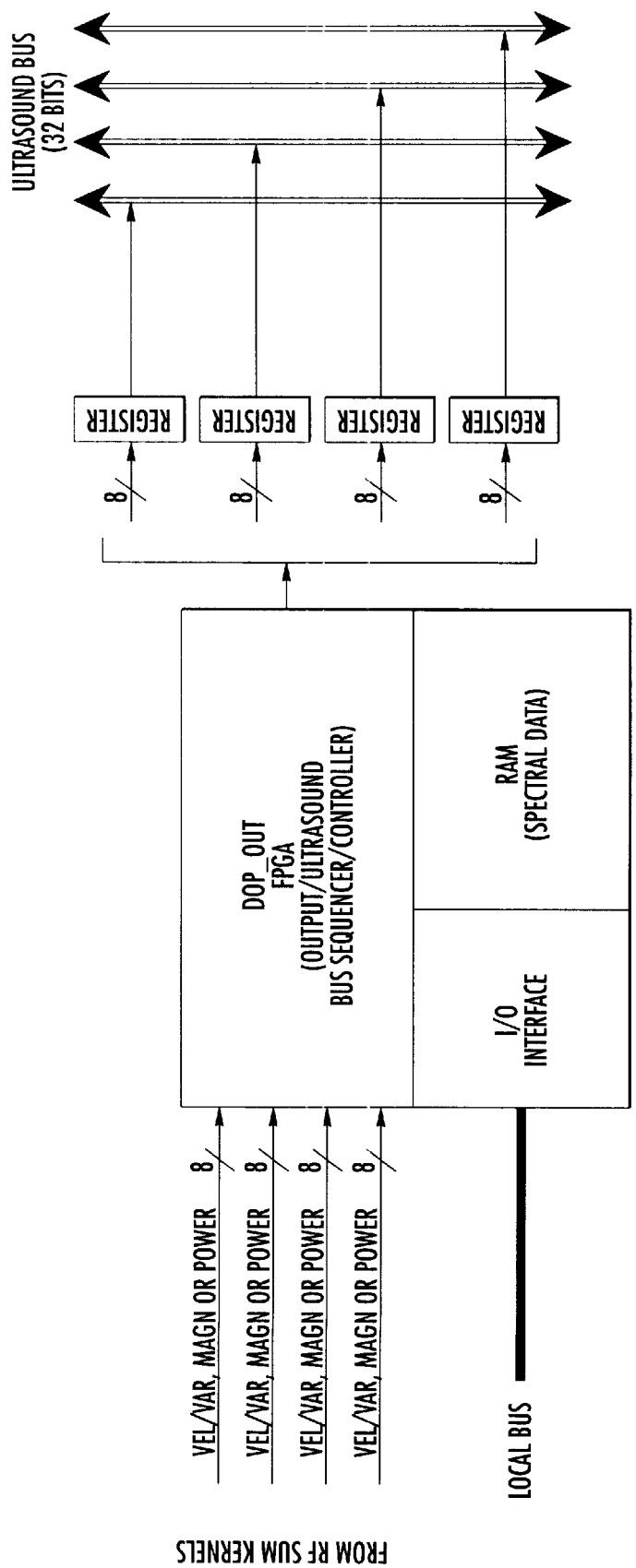
FIG. 8 is a block diagram of an embodiment of an output burst multiplexer shown in FIG. 3B.

The Output Burst Multiplexer 320 is shown in FIG. 8. It includes the Doppler Output FPGA 320 for sequencing of the data flow from the RAM of each of the 16 RF Sum kernels (Color Flow mode), or the FFT Output RAM (Spectral Doppler mode) to the Ultrasound Bus. The output data values from Color Flow, Power Doppler, and Spectral Doppler processing are burst to the Ultrasound Bus upon command from the controlling software via the Doppler Control Register.

The following contains a mathematical description of the Doppler Processing.

Processing performed by the Wall Filter FPGA 405

In-phase: I-data: $[(I_n-C_i)-(R_i-L_i)X_n+(2C_i-(R_i+L_i))XX_n]=Si_n$ with $Avg_i=(\Sigma Si_n)/n$ $Fi_n=Si_n-Avg_i$ Filter outputs for I-data and, Quadrature-phase: Q-data: $[(Q_n-C_q)-(R_q-L_q)X_n+(2C_q-(R_q+L_q))XX_n]=Sq_n$ with $Avg_q=(\Sigma Sq_n)/n$ $Fq_n=Sq_n-Avg_q$ Filter outputs for Q-data where n=sequence number of inner packet value n=1,2,3 . . . (packet size-2)

L=left outlier used in curve fitting
R=right outlier used in curve fitting
C=center value used in curve fitting
$X_n$=X constant value to the 1st power
$XX_n$=X constant value to the 2nd power
$Avg_i$=average of I-data samples over the inner packet values
$Avg_q$=average of Q-data samples over the inner packet values The X-Constants are used in the wall filtering processing. The address space to be written in the each of the Wall Filter FPGAs is a total of 64 locations. The first value is written to the greatest address value, the second is written to the next decremented address, and so on. The X-Constants for a packet size=7 are shown in the table below.

For n=1 to 7,

| $V_n =$ | $-3/3$ | $-2/3$ | $-1/3$ | 0 | $1/3$ | $2/3$ | $3/3$ |
|---|---|---|---|---|---|---|---|
| $VV_n =$ | $(-3/3)^2$ | $(-2/3)^2$ | $(-1/3)^2$ | 0 | $(1/3)^2$ | $(2/3)^2$ | $(3/3)^2$ |
| $X_n =$ | $(1/2) * V_n$ | | | | | | |
| $XX_n =$ | $(1/2) * VV_n$ | | | | | | |
| $1/N =$ | $1/7$ | | | | | | |

Then, order the $X_n$ and $XX_n$ constants from address xxxx 00FC to the lowest address, using up all these constants. Then fill in the remainder of the address space down to xxxx 0000 with the 1/N value, e.g.

$X_1$ address xxxx 00FC
$XX_1$
$X_2$
$XX_2$
. . .
$X_6$
$XX_6$
$X_7$
$XX_7$
1/N
1/N
. . .
1/N address xxxx 0000

| # | Address | Value |
|---|---|---|
| 1 | xxxx 00FC | 0000 D555 |
| 2 | xxxx 00F8 | 0000 1C71 |
| 3 | xxxx 00F4 | 0000 EAAA |
| 4 | xxxx 00F0 | 0000 071C |
| 5 | xxxx 00EC | 0000 0000 |
| 6 | xxxx 00E8 | 0000 0000 |
| 7 | xxxx 00E4 | 0000 1555 |
| 8 | xxxx 00E0 | 0000 071C |
| 9 | xxxx 00DC | 0000 2AAA |
| 10 | xxxx 00D8 | 0000 1C71 |
| 11 | xxxx 00D4 | 0000 1999 |
| 12 | xxxx 00D0 | 0000 1999 |
| 13 | xxxx 00CC | 0000 1999 |
| 14 | xxxx 00C8 | 0000 1999 |
| 15 | xxxx 00C4 | 0000 1999 |
| 16 | xxxx 00C0 | 0000 1999 |
| 17 | xxxx 00BC | 0000 1999 |
| . . . | . . . | 0000 1999 (all) |
| 62 | xxxx 0008 | 0000 1999 |
| 63 | xxxx 0004 | 0000 1999 |
| 64 | xxxx 0000 | 0000 1999 |

Processing Performing by the Velocity/Power FPGA 410

Processing techniques for determining velocity of tissue are discussed, for example, in "*Estimating of blood Velocities Using Ultrasound, A Signal Processing Approach*" by Jorgen Arendt Jensen, Technical University of Den-mark, Cambridge University Press 1996 which is incorporated herein by reference.

Calculated NUM and DEN:

$NUM=(1/N_c)\Sigma(Fi_n)(Fq_{n+1})-(Fi_{n+1})(Fq_n)$ numerator sum $DEN=(1/N_c)\Sigma(Fi_n)(Fi_{n+1})+(Fq_{n+1})(Fq_n)$ denominator sum where $Fi_n$=Wall Filter outputs for I-data
$Fq_n$=Wall Filter outputs for Q-data
n=sequence number of inner packet value; n=1,2,3 . . . p)
p=packet size-2
$N_c$=packet size-3

Calculated Power;

$Psqrd=(1/p)\Sigma[(Fi_n)^2+(Fq_n)^2]$

Power =square root (Psqrd) power over each packet where n=sequence number of inner packet value; n=1,2,3 . . . p
=packet size-2

Calculate Velocity(angle) and Magnitude:
A Cordic algorithm is utilized to compute the magnitude and the angle from the NUM and DEN inputs calculated above.

CORDIC:
If NUM<0
    X[0]=-NUM
    Y[0]=DEN
    THETA[0]=-90 degrees
Else
    X[0]=NUM
    Y[0]=-DEN
    THETA[0]=90 degrees
For i=0 to 15, i++
    If Y[i]<0
        X[i+1]=X[i]-Y[i]
        Y[i+1]=Y[i]+X[i]

```
        THETA[i]=THETA[i]–ATR_constant
    Else
        X[i+1]=X[i]+Y[i]
        Y[i+1]=Y[i]–X[i]
        THETA[i]=THETA[i]+ATR_constant
    End
End
Results:
    True Magnitude=0.607253*X[15]
    Velocity (angle)=THETA[15]
Calculated Variance:
    Variance=1–(True Magnitude)/(Power)
```
The above algorithm is taken from page 206, equation 7.47 of Jensen.

Z-Constant Values for the Velocity/Power Algorithm

The Z-Constants are used for the Cordic processing performed within the Velocity/Power FPGA 410. These values can be stored in read only memory which is programmed at the time the FPGAs are configured. The Z-Constant values may be read as described above herein. The values read are indicated below in the $4^{th}$ column;

| i | Atan($2^{-i}$) degrees | Address (4 least significant hex digits) | Value (hex) Read from ROM in Velocity/Power FPGA |
|---|---|---|---|
| 0 | 45 | F | 2000 |
| 1 | 26.565 | E | 12E4 |
| 2 | 14.036 | D | 09FB |
| 3 | 7.125 | C | 0511 |
| 4 | 3.576 | B | 028B |
| 5 | 1.789 | A | 0146 |
| 6 | 0.896 | 9 | 00A3 |
| 7 | 0.448 | 8 | 0051 |
| 8 | 0.223 | 7 | 0029 |
| 9 | 0.111 | 6 | 0014 |
| 10 | 0.056 | 5 | 000A |
| 11 | 0.028 | 4 | 0005 |
| 12 | 0.014 | 3 | 0003 |
| 13 | 0.007 | 2 | 0001 |
| 14 | 0.003 | 1 | 0001 |
| 15 | 0.002 | 0 | 0000 |

A scan converter 235 receives Doppler data from the Doppler processor 225 and produces an ultrasound image that includes the viewpoints and the Doppler data selected by the user via the interface 210. For example, color flow Doppler data is overlaid on the viewpoint selected by the user via the interface 210. Alternately, grayscale spectral Doppler data is displayed with a horizontal time axis and can be scrolled.

The scan converter 235 will now be described in greater detail.

Scan Converter 235

Figure 9:
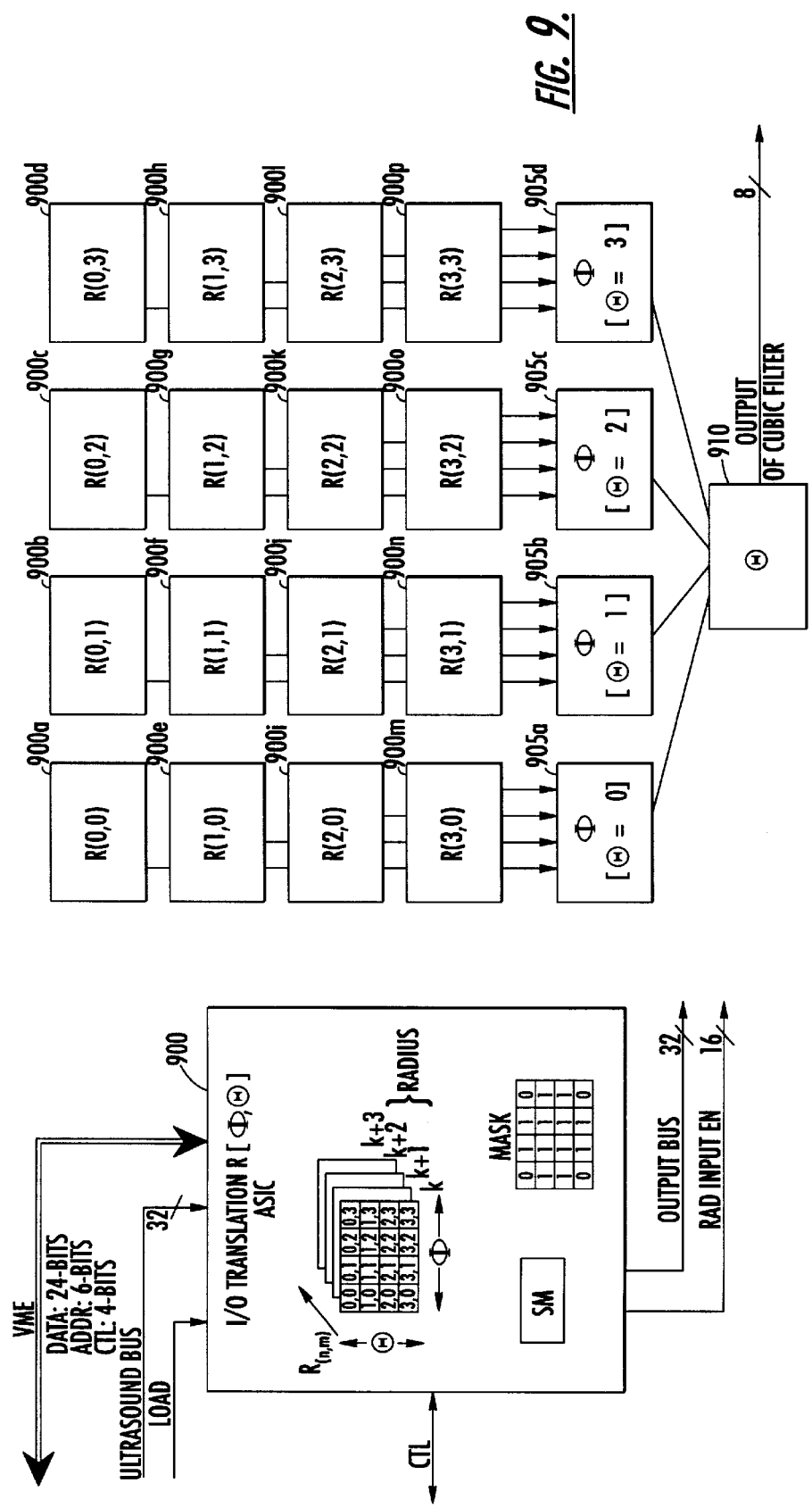
FIG. 9 is a block diagram that illustrates the cubic interpolation processing architecture according to the present invention.

The Scan Converter 235 accepts four bytes of information over the ultrasound bus. The ultrasound data is stored in a buffer with radius (depth) of up to 1024 samples. Receive node parallel processing generates 16 independently steered values for each depth point. The 16 values are interpreted as 4 directions in Θ by 4 directions in Φ (as shown in FIG. 9). The 16 values in Θ and Φ are stored sequentially in memory beginning at a base address supplied by the Real-Time Processor (RTP). Each discrete Θ, Φ value is stored in a unique radius processor element. A 4×4 mask is also programmed by the RTP which enables or disables each Θ, Φ value from being stored in the radius processor element's memory. Dual 32-bit wide buffers store the information so that the Radius Processing FPGAs can simultaneously access 4 sequential radial points on any radius depth modulus of four.

According to FIG. 1, the basic processing kernel is built for 3D cubic interpolation (see FIG. 1). Sixteen Radius processors 900a–p operate on volume data stored in 64-bit wide buffers. Each memory of the sixteen buffers contains an implicit 4×4 Θ, Φ coordinate based on the input storage. Another 5-bits of Θ and Φ addressing per radius processor yields a total of 128×128 angular resolution. Generally, the input memory (per Radius Processor) is set up with 4M-bit memory which yields an entire volume space of 128×128× 1024. The software will usually use an MSB of one of the three dimension (R, Θ or Φ) to page the memory for dual buffering. The radius processor inputs eight data values per sample and selects four sequential radius points based on a 3-bit MUX address provided by the Output Address Generator (OAG) circuit. Generally the four data points per radius processor are cubic interpolated into the desired scanning integer x,y,z coordinate. However, the coefficient tables inside the Radius FPGA may be programmed to apply an average, bilinear (2-point) interpolation, or other 4-point FIR operations. In addition to the 3-bit location address, an additional 8-bit fractional coefficient is always provided by the OAG to locate the 4-points with fractional precision of $\frac{1}{256}$ to the desired z ordinate. Clipping values are provided by the OAG whenever one or more of the scanning radius values are not available from the input acquisition process. In the clipped case the nearest non-clipped value is inserted at the clipped radius point. The scan converter will linearly fade to the outer values of the volume fringes, however, the transparency calculation on the video board utilizing the alpha value supplied by the scan-converter linearly fades the fringes to a programmed background value. The four values are multiplied by the taps chosen in the four respective 256×12-bit Look-Up-Tables (LUTs) and their sum is computed to complete the 4-point FIR in radius for that respective radius point. The radius processors send their 8-bit outputs to four Φ processors 905a–d which provide similar 4-point FIR processing on the planar values output by the radius processor to align the data to the x-ordinate. Finally, the four outputs of the Φ processors 905a–d are fed to a single Φ FPGA 910 to align the four points to the y-ordinate. This output is a rasterized (x,y,z) point interpolated from data acquired in (R, Θ, Φ) space. The Θ and Φ processors apply clipping in an analogous fashion to the way the radius processors apply clipping. The Θ and Φ processors 905a–d, 910 also receive 2-bit MUX information from the OAG which cyclically decodes the data input ordering.

The scan-converter 235 supplies an alpha (or coverage) value which is a measure of the amount of clipping applied on the interpolated result. The coverage value will range from 0 to 128. Zero implies the output is entirely clipped and 128 implies all volume samples were available for cubic interpolation. Therefore, an interpolation with no clipping inserted yields a 128 alpha value and full clipping yields a 0 alpha value. The video processor will utilize the alpha value to blend echo into a programmed background color.

Figure 10:
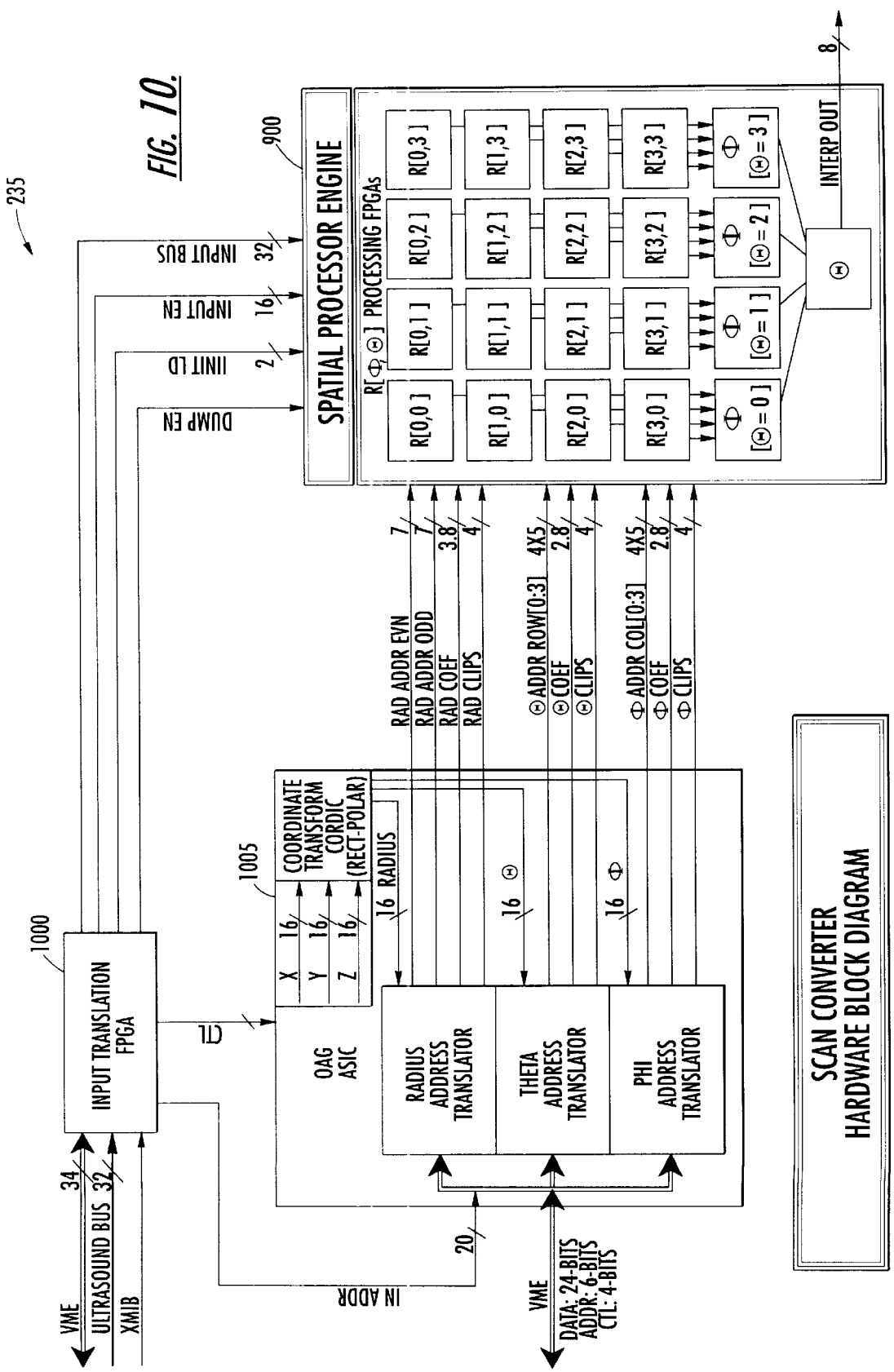
FIG. 10 is a block diagram of an embodiment of the scan converter of FIG. 2.
Figure 12:
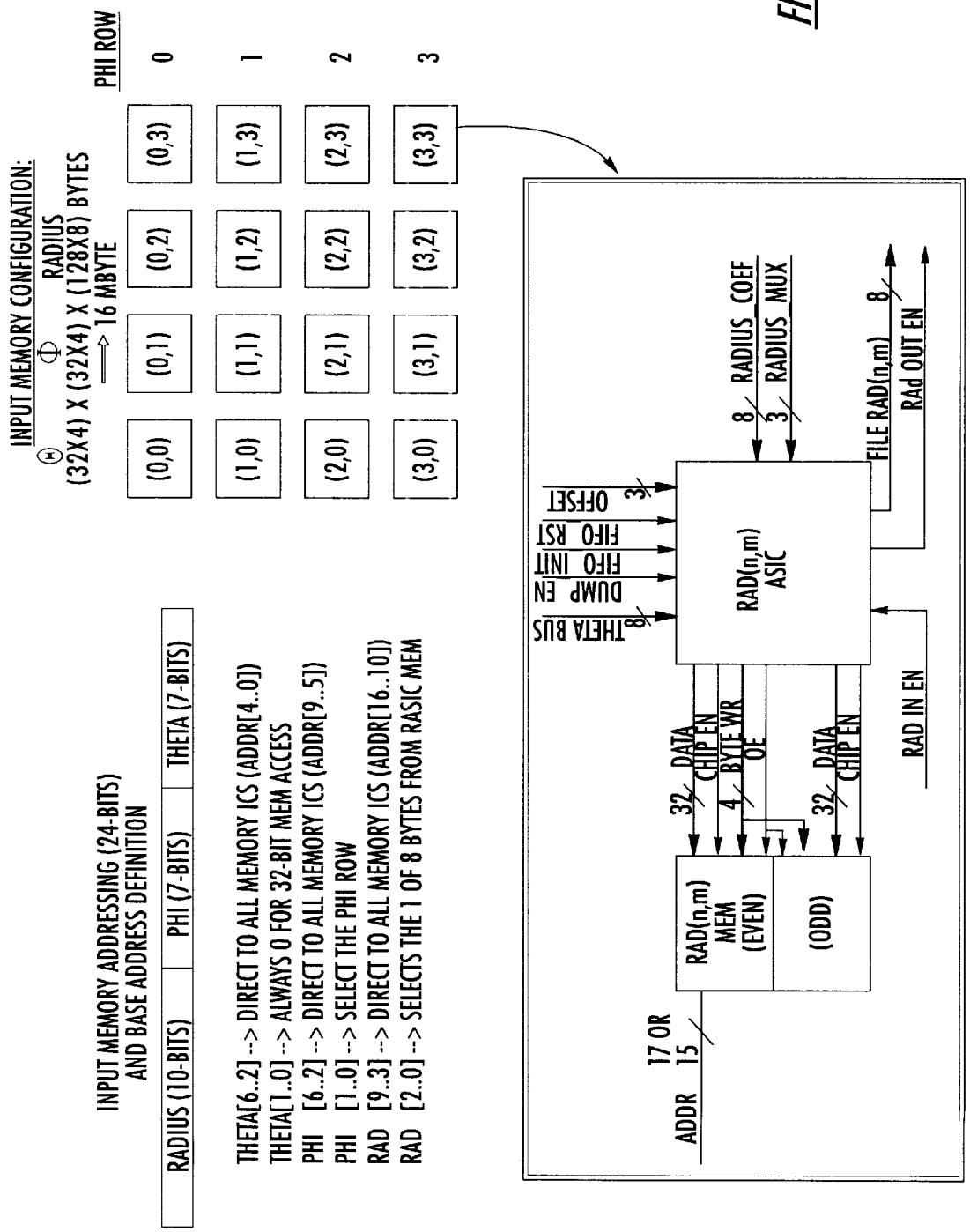
FIG. 12 illustrates an exemplary configuration of memory according to the present invention.
Figure 13:
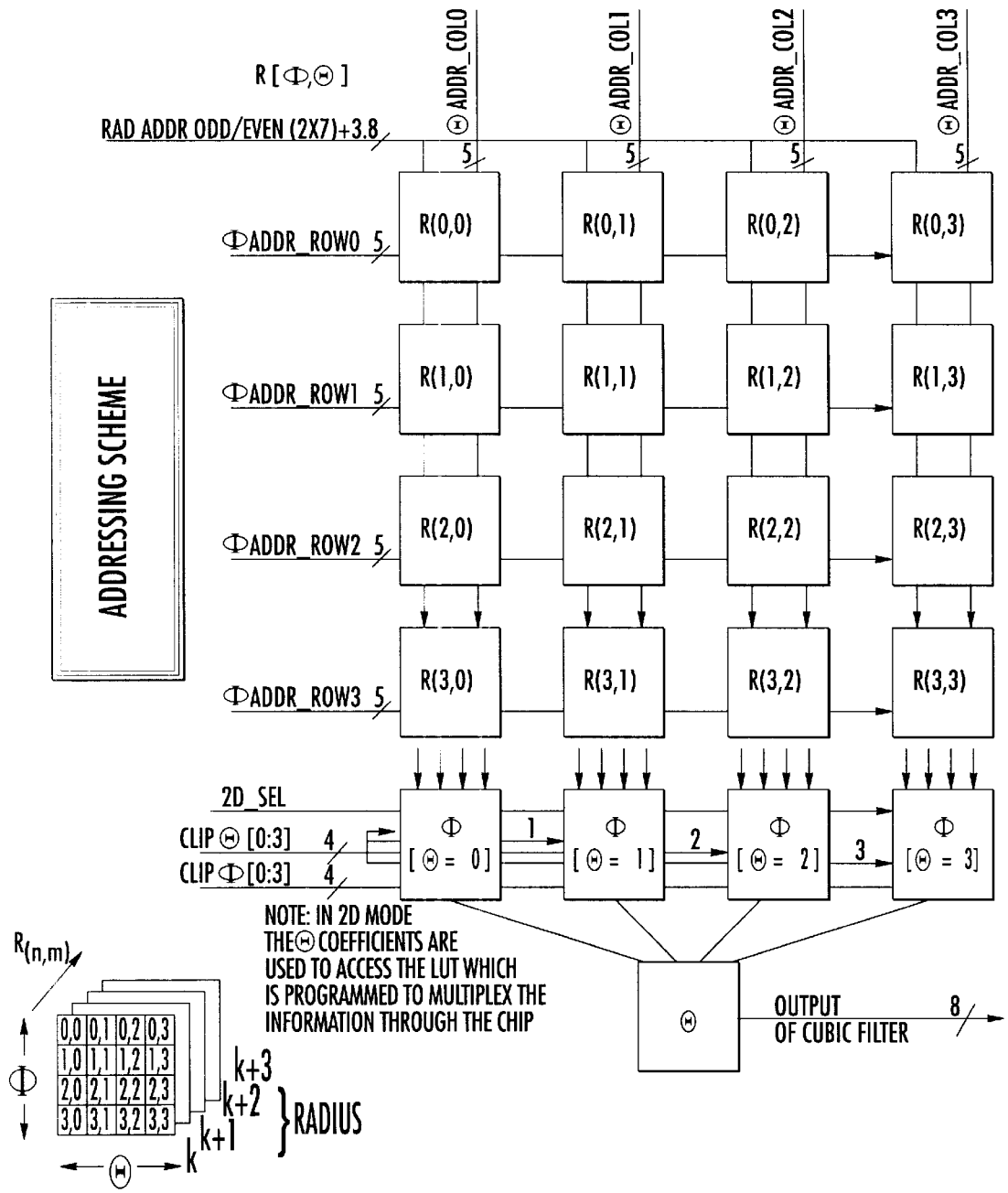
FIG. 13 is a block diagram that illustrates an embodiment of addressing provided to the scan converter shown in FIG. 2.

According to FIG. 10, the input address generator may be software controlled. The radius input buffers are filled with spatially contiguous R, Θ, Φ values of a given scan conversion type. The Output Address Generator (OAG) under software configuration generates the appropriate addresses and controls for the spatial processing engine to cubic interpolate (or other spatial 3D FIR) the x,y,z points. Upon receiving a new volume ready trigger, the OAG 1005 operates from a starting point ($X_0,Y_0,Z_0$) and spatially traces down 3D linear rays by applying dXdU, dYdU, dZdU as it horizontally produces a raster line. Also, if peak detect or averaging of slice planes are implemented the trace will supply N points in the Xn,Yn,Zn space traveling in the dXdW, dYdW, dZdW direction for mean or peak detect computation in the spatial processor 900. As the raster scan lines move down the frame, the $X_0,Y_0,Z_0$ point traverses the dXdV, dYdV, dZdV direction to generate any arbitrary slice in 3D space. Each Cartesian raster point is sent through VLSI rectangular-to-polar circuitry to derive R, $\Theta$, $\Phi$ representations (with fractional resolution). The OAG 1005 applies a programmable scaling factor (multiplication) and offset (addition) to the output of the polar coordinates before supplying R, $\Theta$, $\Phi$ addressing and control to the spatial filter processor The 2D processing unit applies a subset of the 3D spatial processing engine. Addresses from the $\Phi$ direction are borrowed by the $\Theta$ address unit to increase horizontal resolution by a factor of fifteen (2000 angles or <0.05 degree angular resolution). The $\Phi$ processors 905*a–d* are bypassed when the 2D_SEL is activated. The $\Phi$ processors 905*a–d* coefficient is hard-coded to 0xff which applies tap coefficients of 0,1,0,0 to the data. The data is rotated by one so that the desired theta values are effectively passed through the device to the Theta processing element. Since only the cubic interpolation table contains the 0,1,0,0 taps, the cubic interpolation table is selected by the Phi processors. This is done by setting Line Space Scale to the maximum (0xffff).

The spatial processor 900 operates in one of two data width modes and one of two arithmetic modes. The data input may be either 8-bit unsigned (typically echo data) or 8-bit signed (typically color flow). The data input may be two fields of 5-bits signed Color Doppler and 3-bits of unsigned Doppler variance. The hardware implication is that each multiplication path will contain an 8-bit (signed or unsigned) multiplier and a 3-bit (unsigned) multiplier. Note: the 8-bit multiplier uses approximately 8% of a 10K50 device.

The ICTL (Input Controller) 1000 acts as the primary interface to the VME. The OAG (Output Address Generator) 1005 function which also receives parameters from the VME acts as a local peripheral to the ICTL 1000. The ICTL 1000 provides Chip Select decodes to the OAG 1005.

FIG. 10 is a hardware block diagram of the Scan Converter 235. The main functional blocks consist of the spatial processor engine, the Output Address Generator 1005 (OAG) and the Input Address Generator/Input Controller 1000. The following sections will describe the I/O (Hardware and Software) for each of the functional blocks. Input Address Generator/Input Controller Each transmit line the Real-Time Processor (RTP) writes the new base address for the data input and a start position. The base address is the $\Theta$, $\Phi$ position and an offset for the initial data write into the input buffers radial position. Also, software may decide which field's Most Significant Bit (MSB) designates the page bit for double buffering the memory (e.g. for 4Mbit memory 1024×64×128 resolution is possible by utilizing the $\Theta$ Most Significant Address Bit for paging). The starting position is a 4-bit number (constituting the two LSBs of the $\Theta$, $\Phi$ address fields of the input address) that is normally 0 for full explososcan masks, however, for tiling different mask patterns different starting positions are used (see FIG. 3 for example of masking the comers of an explososcan). As the line is acquired, the Input Controller (ICTL) 1000 receives the data over the Ultrasound Bus and writes the data (shifted according to the starting positions) into the Radius Processing (RASICs) FPGAs FIFOs. Each RASIC has a 256×4-byte deep FIFO to store up to an entire line of 1024 bytes. When the current input line has been loaded, the current input line the ICTL 1000 signals the Output Address Generator (OAG) 1005 to freeze the pipelined scan-conversion processing and dump the FIFOs into the RASICs input buffers beginning at the address specified by the base address. The Input Controller will release the OAG 1005 to continue scan-conversion when the FIFO dump is completed. The ICTL 1000 enables the RASICs 900 which have received data during the previous line as defined by the mask. The Input Address is normally the $\Theta$, $\Phi$ position, however when re-focusing, another line may be acquired with different focus parameters which is loaded into the input buffer at a radial address offset. The RASICs 900 utilize the initial address LSBs to interpret which bytes to enable of the 8-byte wide data bus. The input buffer which is 64-bits wide are loaded 32-bits at a time, therefor, a 512 deep line is dumped into the input buffers in 512/4/40 MHz=3.2 usec. Capability for line depths up to 1024 samples are possible with this scan-converter. The input controller ends the input buffer dump after the appropriate number of radius inputs and the scan-conversion process is restarted by the OAG.

The RTP may place the Scan Converter 235 in test mode when scanning is de-activated. In test mode the Ultrasound Bus is ignored and the RTP may read and write the input memory directly. The scan converter memory is configured as 16Mbyte which is read and written 32-bits per access. The memory maps into R, $\Theta$, $\Phi$ space as defined in FIG. 4. Thus the RTP may perform memory testing and load known test patterns when scanning is disabled.

The hardware booted VME FPGA will receive the entire VME Interface (A[31..0], AM[5..0] and CTL) and provide local chip select decode to the ICTL 1000 and OAG 1005. The ICTL 1000 and OAG 1005 receive the 8 address and 24 data lines (thus minimizing I/O). The ICTL 1000 and OAG 1005 FPGA's generate local DTACKs. The VME FPGA will generate a VME DTACK based on reception of the local DTACKs.

The VME FPGA is the only hardware booted FPGA. The other 27 FPGAs are loaded in three separate software downloads of the configuration data.

| Signal Name | Address # - bits | Description |
| --- | --- | --- |
| Input Address | 0x0a00 7000    24 | Bits 23:0    Initial Position for dumping the RASICs FIFOs. |
|  |  | Note: the Input Buffers are effectively 1 Mbyte each Configured as → (128x8)x32x32. |
| MCLK_DIV[3..0] | 4 | Bits 27:24    MCLK_2 divide ratio. The valid divide ratio is 5–12. The programmed value should be N-1. Eg Divide by 5 → Load 4. |
| IGNORE_DSTBB | 1 | Bits 28    Ignore DSTBB. Equivalent to writing Zero to Input Mask! |

-continued

| | | | |
|---|---|---|---|
| INPut_MODE_2D | | 1 | Bits 29   Input Mode 2D |
| Input Mask | 0x0a00 7004 | 16 | Input Mask for Ultrasound ACQuisition |
| ICTL_REG | 0x0a00 7008 | 16 | Scan Converter Control Register |
| ST_SCNV | | R/W SEMA-PHORE | Bit 0   Start Scan Conversion. When a new volume has been received the RTP sets this bit (after reconfiguring the Volume Enables and other control registers if desired) to trigger the scan conversion processing. Scan Conversion will begin immediately if the scan converter is idle or immediately following commencement of the previous volume scan conversion. This bit will be read high until the scan conversion completes processing/checking all 16 viewports. |
| HW_BUSY_EN | | R/W | Bit 1   HW ENable of BUSYB. The first generation scan converter contained dual buffers for processing and input. BUSYB is a hardware hold off which commands the T&C to stop inputting data to the scan-converter until it has finished processing the present volume. This ENable signal allows the new processor to operate the same way. However since the new scan-converter may have multiple buffers for multiple volume types, the RTP may choose to continue receiving data, thus disabling this function. |
| SCNV_ON | | Read Only | Bit 2   SCNV ON. This is a read only status bit which is active when the Scan Converter is processing the present volume. |
| BUSYB | | Read Only | Bit 3   BUSYB. This is a read only status bit which is active low when the Scan Converter is triggered to scan convert the next volume, but it is presently processing the previous volume. Note: If Bit 1 is enabled this is the same signal which drives the T&C logic to disable input data. |
| IGNORE_XMTB | | R/W | Bit 4   IGNORE_XMTB. Setting this bit ignores the pipe-line of Start Scan Conversion until the next line. |

In 2D Mode the Input Mask and Input Address are used to store only the 2D Theta information in the correct Phi Row (see FIG. 4) for 2D processing. The Base Address bits [8:7] (which are the two LSBs of the PHI field) determine which Phi Row to store the 2D data. The Input mask is normally set to 0x000f, however, values less that 0x000f may be used for subset processing. The following lists the settings for the mask and the address bits to fill the input memory in 2D mode:

subsections will describe each element of the spatial processing engine in detail.

The Spatial Filter calculates the spacing between $\Theta$ and $\Phi$ lines for the given radius sample and applies an anti-aliasing filter when the spacing between lines is less than one output sample. The anti-alias filter coefficients are TBD but will be more of a spatial average than the interpolation filtering used when line spacing is greater than one.

| [8:7] | ADDR bits [10:9] : | 00 | 01 | 10 | | 11 | Mask |
|---|---|---|---|---|---|---|---|
| 00 → | Row 0 which stores Theta | 0..127, | 512..639, | 1024..1151 | and | 1536..1663. | 0x000f |
| 01 → | Row 1 which stores Theta | 128..255, | 640..767, | 1152..1279 | and | 1664..1791. | 0x000f |
| 10 → | Row 2 which stores Theta | 256..383, | 768..895, | 1280..1407 | and | 1792..1919. | 0x000f |
| 11 → | Row 3 which stores Theta | 384..511, | 896..1023, | 1408..1535 | and | 1920..2047. | 0x000f |

The Spatial Filter is a processing engine hardware architecture devised for volumetric filtering 4×4×4 cubic spaces. The normal volumetric filtering applied is cubic interpolation which translates volumetric samples in the R, $\Theta$, $\Phi$ space to integer 3D Cartesian plane points. Outputs of the spatial filter may be averaged or peak detected across multiple slice planes before transfer to the video processor. Since the spatial engine is Field Programmable Gate Array (FPGA) logic with programmable coefficient memory, many types of volumetric filters within the 4×4×4 cube may be applied. The spatial processor operates on volume data supplied under the control of the input and output address generating machines. The data is sampled, stored and retrieved from the input buffer memory for the processing engine to coherently filter contiguous data. The following The Radius Processors 900a–p are a 4×4 matrix of FPGAs which operate (as a unit) on the entire 64-sample volume input. Each RASIC FPGA 900 performs a linear 4-point Finite Impulse Response (FIR) filter on 4 of the 64 samples in the radial (or depth) direction. Fractional R, $\Theta$, $\Phi$ precision is provided for the usual case where cubic interpolation filtering is applied. The spatial engine is configured so that each RASIC's 900 input buffer contains all samples (for a given $\Theta$, $\Phi$ in the depth (or Radius) direction. Each adjacent RASIC 900 accesses data with adjacent $\Theta$, $\Phi$ information so that volumetric filtering is applied. The 4×4 set of RASIC FPGAs 900 operating on 4 adjacent radial points creates a cubic array which normally cubic interpolates the radial volume space to a 4×4 planar space in $\Theta$ and $\Phi$. To properly access any four radius points the RASICs 900 are configured so that eight samples are input simultaneously from the input buffer. The Output Address Generator 1005 supplies a 3-bit code which decodes which four (of the eight) samples to utilize in the FIR. In typical operation, each RASIC 900 applies cubic interpolation (in the radial direction) for a given Θ, Φ beam. Each output of the 4×4 kernel of RASICs 900 are passed to the D processors for cubic interpolation in the Φ dimension.

The coefficients for the FIR are signed 12-bits for the 8-bit input samples which may be either signed (Doppler data) or unsigned (echo data and Doppler Variance). The coefficient tables for interpolation (cubic or bilinear) are stored in 256×48-bit memory Look-Up-Table (LUT) contained within the RASIC 900. The 256 deep coefficient memory is selected by the fractional part of the radius (resolution is 1/256) calculation as supplied by the OAG 1005. Interpolation is a symmetric (odd symmetry) tap filter and all of the 48-bit wide coefficients are available simultaneously for 40MHz FIR operation. However, by multiplexing the output of the memories and multiplexing a translation function on the addresses (a one's complement function) the size of the memory can be reduced to 128×48. Thus the upper half of the six memory blocks may contain other filter coefficients (perhaps bi-linear interpolation or averaging coefficients used for color Doppler processing). The Altera 10K50 FPGA's contain 10×256×8-bits of onboard memory, so the 256×48-bit coefficient memory utilizes 6 of the 10 available memory units. When Doppler scan conversion is interleaved with echo scan conversion the Doppler processing applies the same spatial FIR coefficients as the echo processing or incorporate the multiplex/address translation scheme to free ½ of the coefficient memory. Another option is to apply a 4-point fix tap register coefficient which implies Low Pass Filter (LPF) operation for the Doppler data. If another set of volumetric coefficients are used during real-time interleaving of color/echo/spectral/variance information, then the scan-conversion stops for an RTP download period each time the data is switched between the third type of processing with different coefficient tables.

Another function provided by the 4×4 kernel of RASIC FPGA's 900 is to input buffer a line of explososcan information. Since scan-conversion processing memory and speed is a premium, the input buffers are enabled for burst scan-conversion processing each line while the RASIC 900 acts as an input FIFO. After the line of acquisition, scan-conversion is temporarily halted while the 4×4 explososcan is dumped into the input memory in a burst operation. The input line of data is received with a depth up to 1024×8 and the information is stored in 256×4×8-bit FIFO memory. Memory is stored 4×8-bits wide so that the FIFO may be dumped to the input buffer memory 32-bits wide.

Output Address Generator (OAG)

Figure 14:
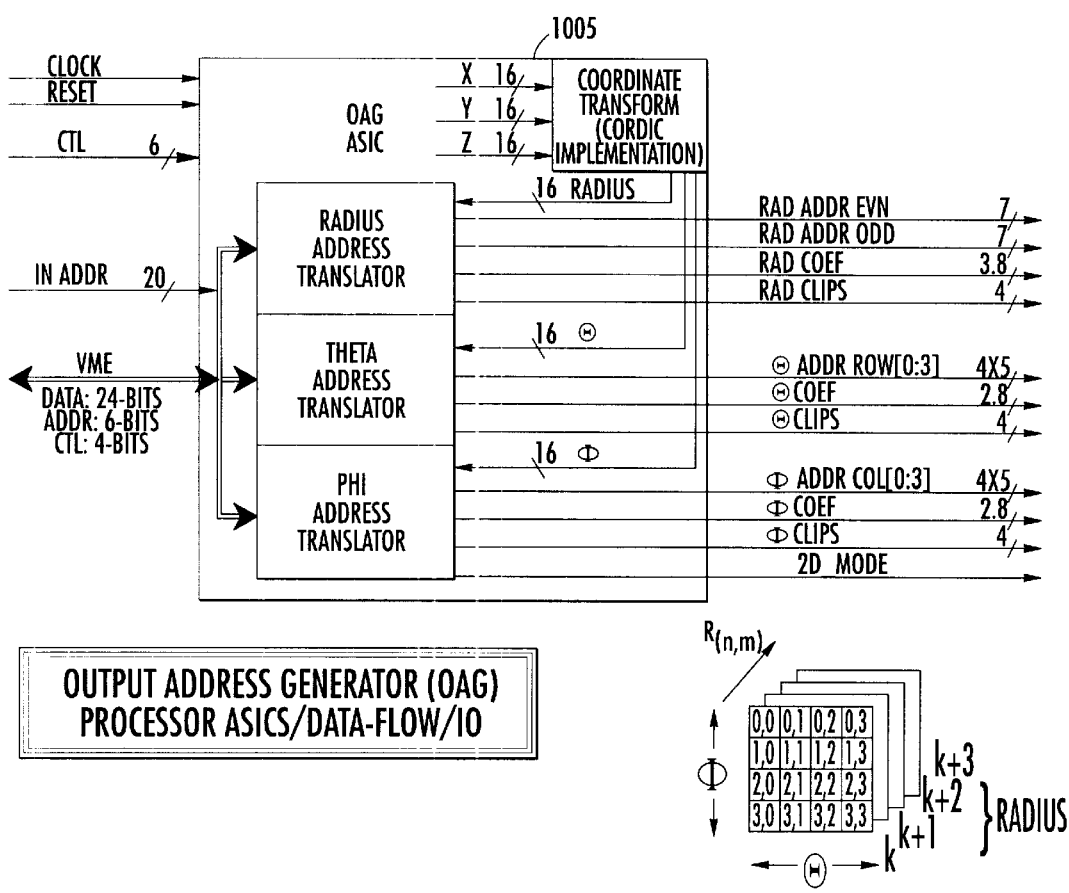
FIG. 14 is a block diagram of an embodiment of an address output generator according to the present invention.

According to FIG. 14, the Output Address Generator 1005 contains programmable sequencing to generate the 3-D Cartesian coordinate points needed for output display. The OAG 1005 converts this point space from the Cartesian domain to the polar coordinate domain (x,y,z→R,Θ,Φ), to spherical domain (x,y,z→Φ,y,z), or a linear non-transformation (x,y,z→x,y,z). The Cartesian address generator is calculated by applying the programmable dU,dV,dW wrt X,Y,Z parameters to a rasterization processing machine. The state machine generates new x,y,z points with (18-bit) fractional resolution. This x,y,z integer point is passed through a rectangular to polar transformation circuit (cordic implementation) to generate the desired (R,Θ,Φ) address with 8-bits of fractional resolution. The R, Θ, Φ computation is used to generate the 10.8-bit Radius addresses, the 3.8-bit positioning (3-bits to choose 4-bytes per 8-bytes input from the input memory) and fractional Radius address is used for the coefficient LUT. Up to 7.8-bits of Θ, Φ addressing are generated and used to form the rest of the input memory addressing. The fractional 8-bits of Θ, Φ are passed to the ΘΦ processing ASICs respectively.

Figure 15:
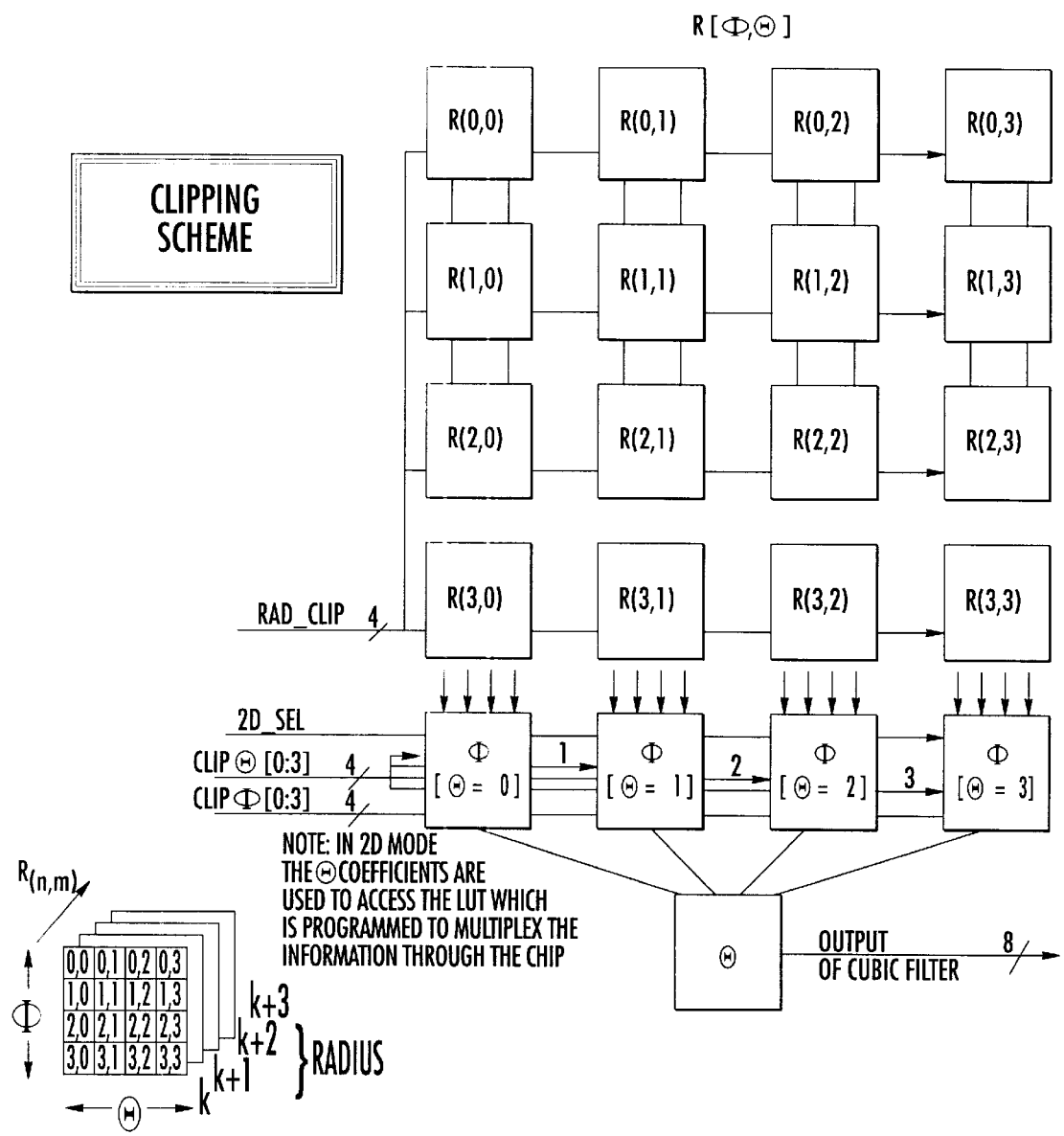
FIG. 15 is a block diagram illustrating a clipping scheme according to the present invention.

The OAG 1005 is programmed with the min/max R, Θ, Φ measurements so that it can apply the clipping signals shown if FIG. 15. The clipping signals are applied discretely to each of the four R, Θ, Φ values generated. When the respective processing element detects a clip for the respective input a pre-defined clip value of zero is multiplexed into the data path prior to filtering.

Figure 16:
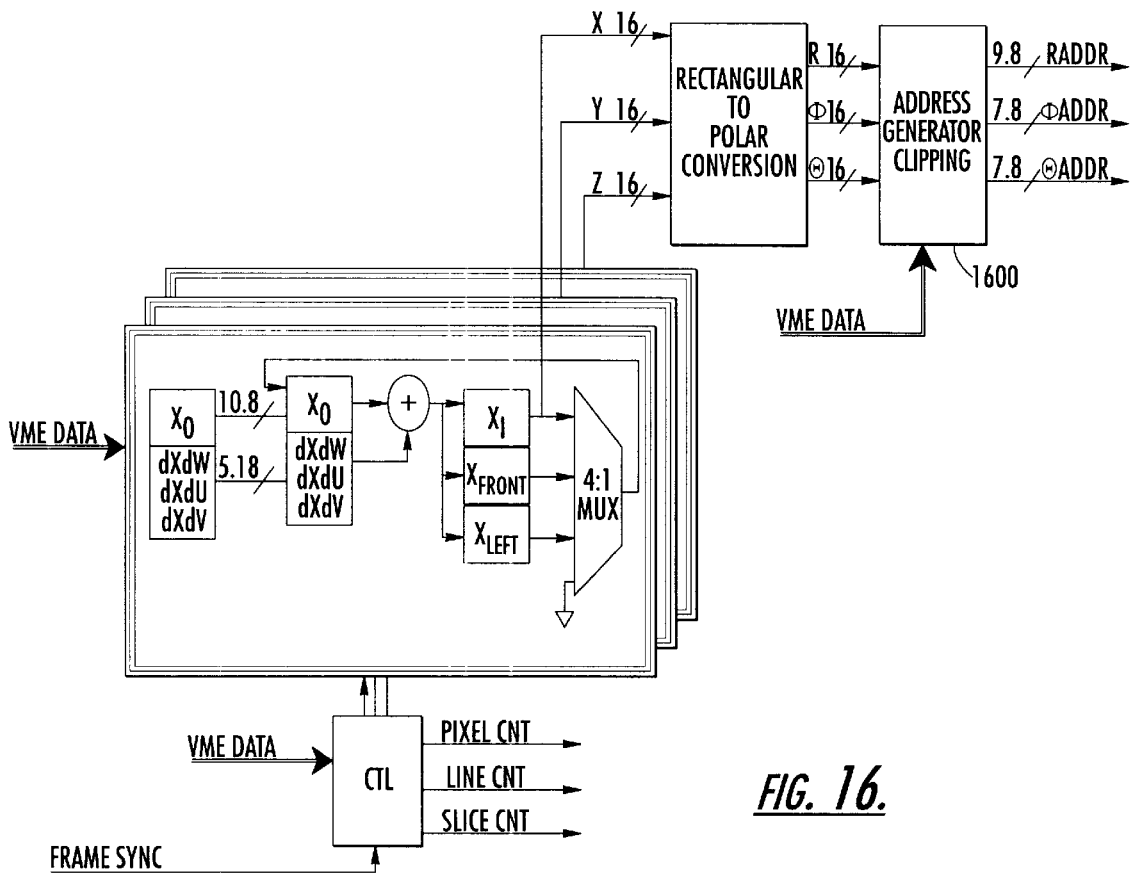
FIG. 16 is a block diagram of an embodiment of the scan converter of FIG. 2.

An OP Code Generator in the OAG 1005 shown in FIG. 16 controls the three dimensional ray tracing of the x,y,z coordinates. The $X_0$, $Y_0$, $Z_0$, dXdW, dXdU, dxdV, dYdW, dYdU, dYdV, dZdW, dZdU, dZdV, dW, dU and dV parameters initialize and control the OP Code Generating state machine which generates any arbitrary three dimensional slice deck through the Ultrasound acquired data with programmable width, length, height and resolution. FIG. 16 is a block diagram of the OAG Address Generator 1005. The Address Generator 1600 processes from the initial point down the stack of slices as specified by the dXdW, dYdW, dZdW parameters. After all slices have been interpolated for the given point the initial slice point is restored and dXdU, dYdU, dZdU parameters are applied to create the next horizontal scan point. After all slices (defined by dW) of all horizontal points (defined by dU) the initial horizontal point is retrieved and dXdV, dYdV, dZdV parameters are applied to generate the first point of the next scan line. This process continues until all lines (defined by dV) have been scan converted. At this point the viewport has been scan converted. The scan-converters state machine checks the next viewport table entry and loads the parameters if the viewport enable bit is set and the Volume Type enable bit is set. If the enable bit is not set the state machine checks the next entry. The scan-converter processes all viewports whose enable bit is set in the table of 32 viewports and enters an idle state if the next acquisition is not ready.

An additional state machine mode is entered if the PROC_dW control bit is set. This mode processes raster scans one slice at a time and then sends the subsequent slice (after a delta depth increment) directly out of the scan converter. This mode is useful for rendering where a large number of slices is processed with depth cueing.

Single Viewport Table (Table has 32 entries→n=0:31)

TABLE 2

Output Address Controller Software Interface

| Signal Name | Address | Units | # bits | Description | |
|---|---|---|---|---|---|
| dW | 0x0a00 0000*n | samples | 10 | bits (9:0) → | # of Scan Slices-1 (Format 10.0 Unsigned) |
| | | | | bits (13:10) → | 0 Pass Slices through |
| | | | | | → 4 Peak Detect Slices |
| | | | | | → 8+ Average Slices |

TABLE 2-continued

Output Address Controller Software Interface

| Signal Name | Address | Units | # bits | Description |
|---|---|---|---|---|
| | | | | → 0.3 AVG Length: |
| | | | | → c IIR Filter Rays ($\alpha = 0.5$) |
| | | | | 2, 4, 8 or 16 |
| CYLINDRICAL VIEWport_TYPE | where *n → Viewport # x 0x40 | | | bit 15 → CYLINDRICAL_MODE bits (17:16) → 00: Echo 01: Dop1: CF/VAR 10: Dop2: Power |
| VOLUME Select | | | | bits (19:18) → 00: Utilize Volume A 01: Utilize Volume B 10: Utilize Volume C 11: Utilize Volume D |
| PROC_dW | | | 4 | bit 20 → 0: Process as Rays 1: Process as Stack (dW-1) Slices |
| 2D_MODE | | | 2 | bit 21 → 2D_MODE (otherwise 3D Mode Selected) |
| POLAR_LINB Enable | | | 2 | bit 22 → POLAR (otherwise LINEAR Mode Selected) bit 23 → Enable Viewport N |
| dU | 0x0a00 0004*n | samples | 10 | # of Horizontal Scan Pixels-1 (Format 10.0 Unsigned). |
| dV | 0x0a00 0008*n | samples | 10 | # of Vertical Scan Lines-1 (Format 10.0 Unsigned) |
| X0[23..0] | 0x0a00 0010*n | samples | 24 | Initial X coordinate starting position (Format: 2's Complement 11.13) |
| dXdW | 0x0a00 0014*n | samples | 24 | delta X wrt W (Format: 2's Complement 6.18) |
| dXdU | 0x0a00 0018*n | samples | 24 | delta X wrt U (Format: 2's Complement 6.18) |
| dXdV | 0x0a00 001C*n | samples | 24 | delta X wrt V (Format: 2's Complement 6.18) |
| Y0[23..0] | 0x0a00 0020*n | samples | 24 | Initial Y coordinate starting position (Format: 2's Complement 11.13) |
| dYdW | 0x0a00 0024*n | samples | 24 | delta Y wrt W (Format: 2's Complement 6.18) |
| dYdU | 0x0a00 0028*n | samples | 24 | delta Y wrt U (Format: 2's Complement 6.18) |
| dYdV | 0x0a00 002C*n | samples | 24 | delta Y wrt V (Format: 2's Complement 6.18) |
| Z0[23..0] | 0x0a00 0030*n | samples | 24 | Initial Z coordinate starting position (Format: 2's Complement 11.13) |
| dZdW | 0x0a00 0034*n | samples | 24 | delta Z wrt W (Format: 2's Complement 6.18) |
| dZdU | 0x0a00 0038*n | samples | 24 | delta Z wrt U (Format: 2's Complement 6.18) |
| dZdV | 0x0a00 003C*n | samples | 24 | delta Z wrt U (Format: 2's Complement 6.18) |
| Angle_Scale for $\Theta$ | 0x0a00 2000*n | lines | 20 | Angle Scale Factor (Format: Unsigned Mag 12.8) |
| Angle_Scale for $\Phi$ | 0x0a00 2010*n | lines | 17 | Angle Scale Factor (Format: Unsigned Mag 9.8) |
| RAD_ALIAS | 0x0a00 4000*n | samples | 16 | Line Space Scale Factor (Format: Unsigned Mag 11.5)[3] |
| SKIN_Offset | 0x0a00 4004*n | samples | 14 | SKIN OFFSET in Samples (Format: Unsigned Mag 10.4) |
| RAD_MAX | 0x0a00 4008*n | samples | 12 | MAXimum Radius in Samples (Format: Unsigned Mag 12.0) |
| Line_Space for $\Theta$ | 0x0a00 4010*n | | 16 | Line Space Scale Factor for (Format: Unsigned Mag 0.15)[2] |
| Line_Space for $\Phi$ | 0x0a00 4014*n | | 16 | Line Space Scale Factor for (Format: Unsigned Mag 0.15)[2] |
| THETA_Offset | 0x0a00 2004*n | lines | 15 | THETA OFFSET in Addresses (Format: 2's Complement 12.4) Add to 2's Comp THETA Computation to Convert to THETA ADDR. THETA ADDR 0 is the Most Negative THETA ray. |
| THETA_MAX | 0x0a00 2008*n | lines | 11 | MAXimum THETA ADDR (Format: Unsigned Mag 11.0) |

TABLE 2-continued

Output Address Controller Software Interface

| Signal Name | Address | Units | # bits | Description |
|---|---|---|---|---|
| PHI_Offset | 0x0a00 2014*n | lines | 11 | PHI OFFSET in Addresses (Format: 2's Complement 8.4) Add to 2's Comp PHI Computation to Convert to PHI ADDR. PHI ADDR 0 is the Most Negative PHI ray. |
| PHI_MAX | 0x0a00 2018*n | lines | 7 | MAXimum PHI ADDR (Format: Unsigned Mag 7.0) |

The THETA_MAX and THETA_OFFset are 11 bits (4-bits more than the PHI parameters) for 2D Mode Processing. In 3D mode the upper 4-bits of the THETA parameters are ignored.

The Line Space Scale is the length of an arc between two adjacent lines at a depth of 2048 pixels. This value is unsigned 0.15 normalized to 1. Normalization to 1 implies that 0x7fff is 2048 at a depth of 2048, 512 at depth 512, etc. This number is multiplied by the unsigned 11.5 number to produce an 11.5 result. The result is compared to 1.0 and numbers smaller than 1.0 are filtered with an anti-alias filter (versus the normal cubic interpolation filter). Typical number for 480×640 raster scan-resolution with 64 lines in Θ and Φ (~1 degree resolution) are ~10 samples per arc at maximum depth of 512 samples which implies 10/512*2^15=0x280. Loading 0x280 will anti-alias until the Radius depth is >51.2 samples. The length between arcs (for a given radius) is computed by:

LineSpaceScale=sin(angular_separation)*2^15

LineSpace=LineSpaceScale*Radius

The Line Space Scale operates on the 11.5 Radius before the SKINOFFSET is applied, however, clips and addresses are generated after SKINOFFSET is applied.

The following register block is preloaded in the paging scheme each time a volume is filled. The input memory will be loaded into one of four logically different volume storage areas. The RTP loads the new A,B,C or D address offset (Paging) before the new volume is loaded. Also to make the processing more versatile the RTP has an enable bit for each of the volumes which will command the viewport processor to skip the given viewport if the volume enable bit is deselected. The Volume Enable is set by the RTP before a new Viewport commences processing.

The RTP pre-programs the SOF_EN bit before commencing scan-conversion on the beginning of a video frame and EOF_EN before scan-conversion completes viewport processing at the end of a video frame.

TABLE 3

Volume Control Interface

| Signal Name | Address | # bits | | Description |
|---|---|---|---|---|
| VOL A PAGING (OAGR) | 0x0a00 5000 | 16 | bits 6..0 → bits 11..8 → bits 15..12 → | Logical Radius Offset for Volume A Logical Theta Offset for Volume A Logical Phi Offset for Volume A |
| VOL B PAGING (OAGR) | 0x0a00 5004 | 16 | bits 6..0 → bits 11..8 → bits 15..12 → | Logical Radius Offset for Volume B Logical Theta Offset for Volume B Logical Phi Offset for Volume B |
| VOL C PAGING (OAGR) | 0x0a00 5008 | 16 | bits 6..0 → bits 11..8 → bits 15..12 → | Logical Radius Offset for Volume C Logical Theta Offset for Volume C Logical Phi Offset for Volume C |
| VOL D PAGING (OAGR) | 0x0a00 500C | 16 | bits 6..0 → bits 11..8 → bits 15..12 → | Logical Radius Offset for Volume D Logical Theta Offset for Volume D Logical Phi Offset for Volume D |
| VOL A..D EN (OAG1) Read Either 0x0a00 1000 or 0x0a00 1004 returns composite 16-bit REG | 0x0a00 1000 | 15 | bit 0 → bit 1 → bit 2 → bit 3 → bit 12 → bit 13 → bit 14 → | Enable Bit for Volume A Enable Bit for Volume B Enable Bit for Volume C Enable Bit for Volume D Spare - Test Point (J36-18) SOP (Start Of Frame) EN - CMD Clear Input Buffer EOF (End Of Frame) EN - CMD Swap Vid Pointers |
| PARAM (OAG1) | 0x0a00 1004 | 1 | bit 15 → | PARAM EN |

FIGS. 17 and 18 illustrate exemplary operations of the OAG 1005 for a specific scan point.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A method of targeting tissue in a volume, the method comprising:

displaying a first image of a first tissue in a first dimension of the volume and a line that extends in a first direction towards the first tissue targeting the second tissue by changing the line on the display so that the line extends in a second direction in the first image towards the second tissue; and displaying a second image of the second tissue in a second dimension of the volume that includes the second line.

2. The method of claim 1 further comprising the step of:

determining a velocity associated with the second tissue at an intersection of the line and the second tissue.

3. A method of determining velocity measurements comprising:

displaying a first image of a first tissue and a second tissue in a first dimension of a volume and a line that extends in a first direction towards the first tissue;

changing the line on the display so that the line extends in a second direction towards the second tissue; and then displaying a second image of the second tissue in a second dimension of the volume that includes the line.

4. A method according to claim 3 further comprising:

determining a velocity associated with the second tissue at an intersection of the line and the second tissue.

5. A method according to claim 4 further comprising:

generating an ultrasound image of the velocity.

6. A method according to claim 5, wherein the act of generating comprises generating the ultrasound image of the velocity as a function of time.

7. A method according to claim 5, wherein the act of generating comprises generating a color flow map of the velocity of the second tissue.

8. A method according to claim 4, wherein the act of determining comprises:

receiving ultrasound data that corresponds to the second tissue; and processing the received ultrasound scan data to provide Doppler data.

9. A method according to claim 3, wherein the act of displaying a first image is preceded by aiming the line in the first direction in the first image.

10. A method according to claim 3, wherein the first dimension comprises an azimuth dimension and the second direction comprises an elevation dimension.

11. A method of determining velocity measurements comprising:

displaying a first image of a first tissue and a second tissue in a first dimension of a volume and first and second indicia that define a line that extends in a first direction towards the first tissue;

changing at least one of the first and second indicia that define the line on the display so that the line extends in a second direction towards the second tissue; and then displaying a second image of the second tissue in a second dimension of the volume that includes the line.

12. A method according to claim 11 further comprising:

determining a velocity associated with the second tissue at an intersection of the line and the second tissue.

* * * * *